United States Patent [19]

Rao et al.

[11] Patent Number: 5,795,958

[45] Date of Patent: Aug. 18, 1998

[54] LIBRARY OF GLYCO-PEPTIDES USEFUL FOR IDENTIFICATION OF CELL ADHESION INHIBITORS

[75] Inventors: Narasinga Rao, Alameda, Calif.; Morten Meldal, Måløv; Klaus Bock, Hørsholm, both of Denmark; Ole Hindsgaul, Edmonton, Canada

[73] Assignee: Glycomed Corporation, Alameda, Calif.

[21] Appl. No.: 664,303

[22] Filed: Jun. 10, 1996

Related U.S. Application Data

[63] Continuation of Ser. No. 134,958, Oct. 12, 1993, abandoned.

[51] Int. Cl.⁶ ........................................................ A61K 38/06
[52] U.S. Cl. ............................ 530/331; 530/322; 514/18
[58] Field of Search .............................. 514/14–18; 530/322, 530/327–331

[56] References Cited

U.S. PATENT DOCUMENTS

| | | | |
|---|---|---|---|
| 4,386,026 | 5/1983 | Ponpipon | 260/112.5 |
| 4,719,289 | 1/1988 | Kolar | 530/331 |
| 4,833,092 | 5/1989 | Geysen | 436/501 |
| 5,194,392 | 3/1993 | Geysen | 436/518 |
| 5,300,492 | 4/1994 | Haviv | 514/15 |
| 5,304,640 | 4/1994 | Lasky | 536/23.5 |

FOREIGN PATENT DOCUMENTS

| | | |
|---|---|---|
| WO 86/05803 | 10/1986 | WIPO |
| WO 90/15070 | 12/1990 | WIPO |
| WO 91/17271 | 11/1991 | WIPO |
| WO 91/18980 | 12/1991 | WIPO |
| WO 91/19818 | 12/1991 | WIPO |
| WO 92/06176 | 4/1992 | WIPO |
| WO 93/20242 | 10/1993 | WIPO |

*Primary Examiner*—David Luxton
*Attorney, Agent, or Firm*—Lyon & Lyon LLP

[57] ABSTRACT

Glycopeptides having the following structure are described:

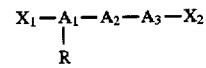

wherein: $X_1$ is hydrogen, an acetyl group, an acyl group or amino acid; R is α-L-fucose, α-D-fucose, β-L-fucose or β-D-fucose, wherein R is O-glucosidically linked to $A_1$; $A_1$ is serine, threonine, tyrosine, hydroxyproline, asparagine, glutamine, homoserine and hydroxylysine; $A_2$ is a glycine, an L-amino acid, a D-amino acid or a modified amino acid; $A_3$ is L or D aspartic acid, glycine or glutamic acid; and $X_2$ is a hydroxyl, an amine or an amino acid.

7 Claims, 30 Drawing Sheets

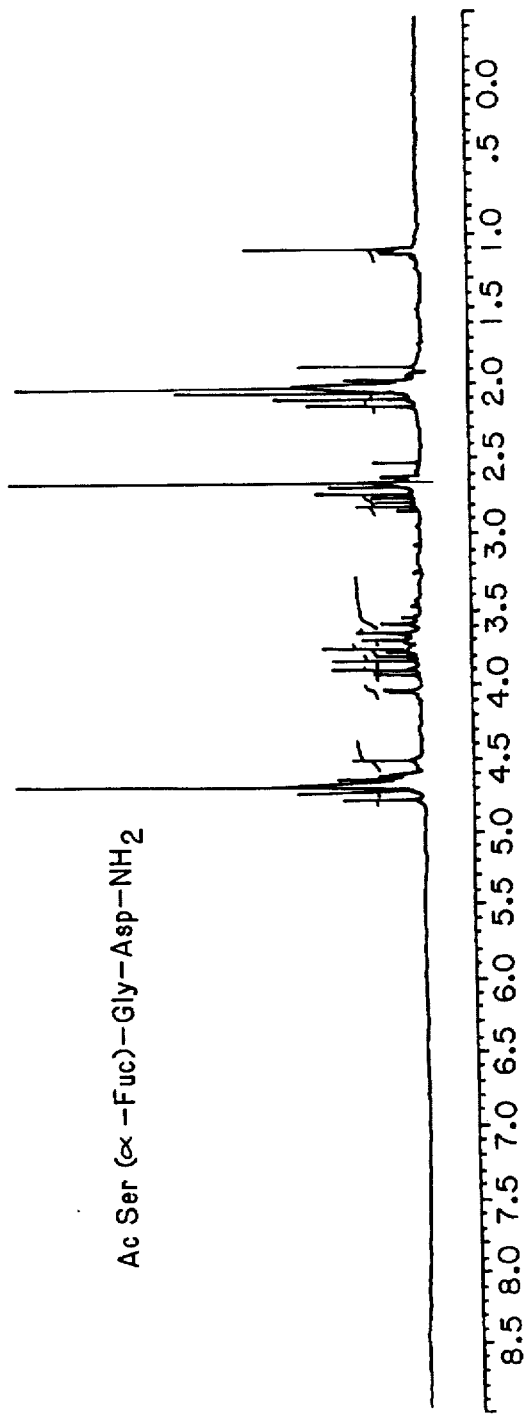
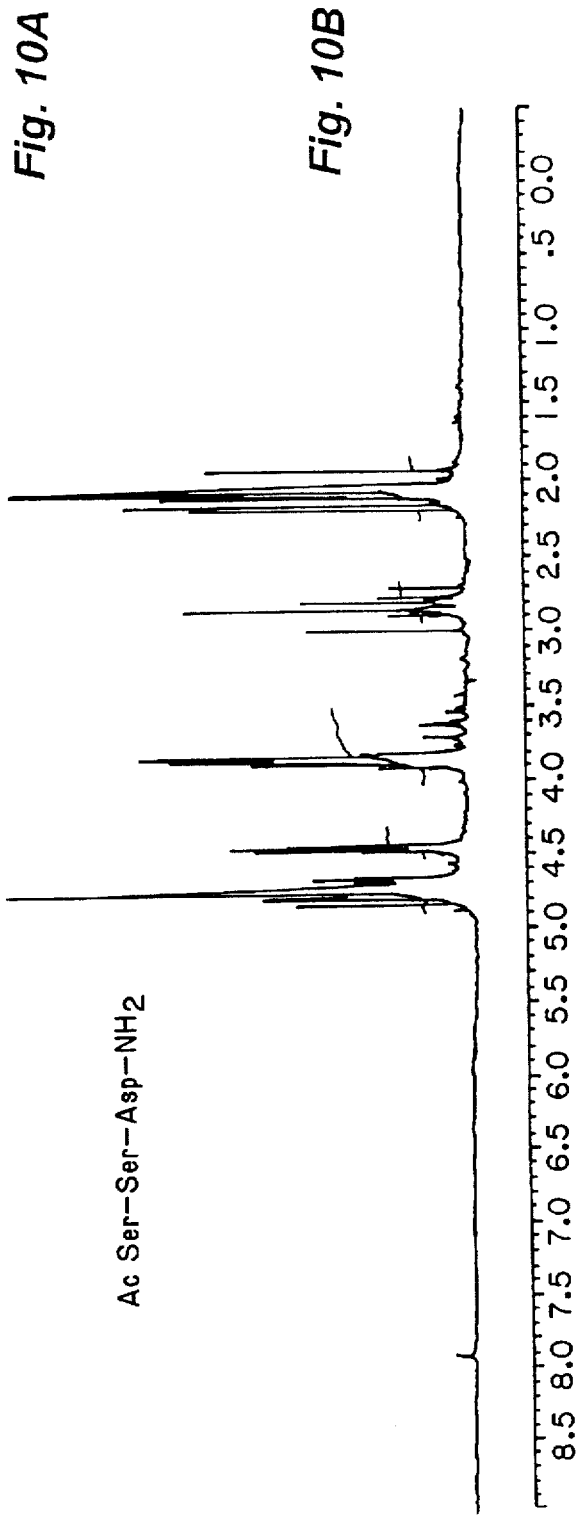
Fig. 10A  Ac Ser(α-Fuc)-Gly-Asp-NH₂
Fig. 10B  Ac Ser-Ser-Asp-NH₂

Ac Ser (βFuc) Arg-Asp-NH$_2$

Ac Ser (αFuc) Arg-Asp-NH$_2$

LIBRARY OF GLYCO-PEPTIDES USEFUL FOR IDENTIFICATION OF CELL ADHESION INHIBITORS

This application is a Continuation-In-Part of application Ser. No. 08/124,958, filed on Oct. 12, 1993, now abandoned.

FIELD OF THE INVENTION

The present invention relates generally to a collection or library of bio-oligomers. The bio-oligomer of this invention is a glyco-peptide. The invention relates to the use of glyco-peptides to identify lectins or carbohydrate binding proteins. The invention also relates to the use of glyco-peptides to identify and characterize inhibitors of cell adhesion. More specifically, the invention relates to the use of glyco-peptides to identify and characterize selectin binding inhibitors.

BACKGROUND OF THE INVENTION

Recognition and binding of ligands regulate almost all biological processes such as immune recognition, cell signalling and communication, transcription and translation, intercellular signaling and enzyme catalysis. There is a longstanding interest in the art to identify molecules which act as agonists or which can agonize or antagonize the activities of peptide ligands such as hormones, growth factors and neurotransmitters.

Scientists have long hypothesized about the role of carbohydrates in intracellular signaling and communication and, in particular, cellular adhesion. Cellular adhesion is a basic biomolecular process involved in many aspects of development including: initiation of fertilization, induction of differentiation, growth control and cell migration (Frazier et al. (1979) *Ann. Rev. Biochem.* 48:491). Compounds that alter cell-cell adhesive interactions have many potential medical applications including use as anti-infectives, anti-inflammatories, contraceptives, etc. Recently, a new group of cell surface lectins involved in cell adhesion, the LEC-CAMs or selectins, have been identified. The selection family of receptors have been implicated in the initial interactions between leukocytes and vascular endothelia leading to lymphocyte homing, platelet binding and neutrophil extravasation (Hallman et al., (1991) *Biochem. Biophys. Res. Commun.* 174:236–243; Lawrence et al., (1990) *Cell* 65:859–873; Luscinskas, et al., (1989) *J. Immunol.* 142:2257–2263). The selectin family of receptors includes L-selectin, involved in lymphocyte homing to peripheral lymph nodes; P-selectin, which participates in adhesion of activated platelets and E-selectin which appears to facilitate T-cell infiltration at sites of cutaneous inflammation. (Picker et al., (1991) *Nature* 349:796–799; Shimizu et al. (1991) *Nature* 349:799–802).

A number of selectins bind to oligosaccharides terminating in the Sialyl Lewis X (SLex) or Sialyl Lewis A sequence. Although there is disagreement as to whether Lewis A (Le-a) or non-sialylated LeX also bind, it is fairly well established that fucose is required for binding. This finding suggests that the combining site of the selectin protein must make a critical interaction with the fucose residue. Therefore, the probability of success in designing an inhibitor of this interaction might be greatly increased if a fucose moiety was incorporated into the structure. This ligand-selectin interaction might be further strengthened by the addition of peptide based molecular structure (scaffolding) which might interact favorably with protein structure in or near the selectin binding site (not at all necessarily mimicking the binding of SLex and not necessarily binding in the same place). If this peptide scaffolding were designed to interact favorably with the selectin, then an inhibitor could be conceived that might possess the same specificity as elements such as SLex and possibly bind even tighter.

The development of pharmaceutical agents keyed to receptor binding sites, however, has been greatly hampered by the difficulty in determining the structure of the peptide ligands. The sheer number and variety of such peptide sequences has made this development an unattainable goal on any basis except by laboriously isolating a specific complex and identifying the structure of the ligand (potential drug). The problem is further complicated by the fact that often the ligand consists of amino acid residues that are not contiguous in the primary sequence.

Recently, there have been several reports on the preparation of peptide libraries and their use in identifying peptide ligands that can bind to acceptors. One approach uses recombinant bacteriophage to produce large libraries. Using the "phage method" (Scott and Smith, 1990, *Science* 249:386–390; Cwirla, et al., 1990, *Proc. Natl. Acad. Sci.*, 87:6378–6382; Devlin et al., 1990, *Science*, 249:404–406), very large libraries can be constructed. The genetic code and the biological system, however, imposes severe inherent limitations on the versatility and diversity of the library. A second approach uses primarily chemical methods, of which the Geysen method (Geysen et al., 1986, *Molecular Immunology* 23:709–715; Geysen et al. 1987, *J. Immunologic Methods* 102:259–274) and the recent method of Fodor et al: (1991, *Science* 251, 767–773) are examples. The methodology of Geysen et al. provides for a limited number of peptides ($10^3$–$10^4$) that can be synthesized on polyethylene pins in a few days. The method of Fodor et al. utilizes a "light-directed spatially addressable parallel chemical synthesis" technique. This technique is also limited by the relative lack of development of photochemical peptide synthesis methods.

Large scale parallel concurrent peptide synthesis techniques have also been developed. Houghton reported synthesizing hundreds of analogous peptides simultaneously in polypropylene mesh packets (tea bag method) (Houghton, 1985, *Proc. Natl. Acad. Sci.*, 82:5131–5135). Berg et al. (1989, *J. Am. Chem. Sci.* 111:8024–8026) reported a novel polystyrene-grafted polyethylene film support that is suitable for peptide synthesis in parallel fashion. Both techniques used standard Boc amino acid resin with the standard deprotecting, neutralization, coupling and wash protocols of the original solid phase procedure of Merrifield (1963, *J. Am. Chem. Sci.* 85:2149–2154).

A parallel multiple column peptide synthesizer which operates exclusively by the distribution of solutions into a Teflon block containing 96 column reactors arranged in an Elisa-type arrangement has been described (Holm, A., et al., 1989 *Peptides* 1988 (G. Jung and E. Bayer, eds.) Walter de Gruyter, Amsterdam). The preparation of building blocks $N^\alpha$-Fmoc-Ser(Ac$_3$-α-D-GalpNAc)-OPfp and $N^\alpha$Fmoc-Thr (Ac$_3$-α-D-GalpNAc)-OPfp and their application in a simultaneous multiple-column solid-phase synthesis of multiple O-glycopeptides has been described (Peters et al., 1992, *J. Chem. Soc. Perkin Trans* 1:1163–1171).

An apparatus for the parallel synthesis of a large number of peptides having overlapping amino acid sequences and constituting part of a longer peptide chain has been developed (PCT/DK89/00206).

A random bio-oligomer library, consisting of all possible combinations of monomer peptide, oligonucleotide or chimeric peptide-oligonucleotide constructs has been proposed (PCT/US91/04666). The library is screened by introducing an acceptor or substrate molecule of interest to the library such that the acceptor molecule recognizes and binds to one or more solid phase support/bio-oligomer species within the library. The solid phase support/bio-oligomer combination that exhibits the desired property is isolated and the bio-oligomer sequenced for specific identification.

Although useful, none of the procedures developed to date combine the flexibility of a random collection of bio-oligomers or a bio-oligomer library with the specificity of potentially critical peptide modifications. In particular, none of the procedures thus far developed utilize the specificity offered by glyco-peptides.

There is thus a need in the art for a collection or a library of peptide sequences to which a carbohydrate is covalently attached for the isolation of specific lectins or carbohydrate binding proteins including selectin binding inhibitors. Such a library or collection of peptides would combine the flexibility and ease of the screening of a random peptide library, with the specificity offered by the attachment of peptide scaffolding to a critical carbohydrate residue.

SUMMARY OF THE INVENTION

The present invention is directed toward a collection or a library of glyco-peptide templates as well as to methods of use of the glyco-peptides to identify specific biological acceptor molecules.

One aspect of the current invention is a glyco-peptide having the structure:

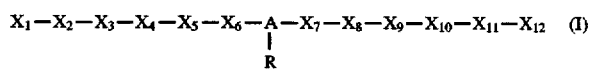

$$X_1-X_2-X_3-X_4-X_5-X_6-A-X_7-X_8-X_9-X_{10}-X_{11}-X_{12} \quad (I)$$
$$|$$
$$R$$

wherein A is an amino acid, preferably an amino acid selected from the group consisting of serine, threonine, tyrosine, hydroxyproline, homoserine and hydroxylysine or asparagine and glutamine;

wherein R is a carbohydrate, preferably a carbohydrate selected from the group consisting of fucose, glucose, N-acetylglucosamine, galactose, arabinose, N-acetylgalactosamine and sialic acid;

In a preferred embodiment of glyco-peptide I, A is serine, R is O-glucosidically linked to said serine and the subunits of $X_1$ to $X_{12}$ are selected from the group consisting of D and L alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, hydroxyproline, hydroxylysine and non-genetically encoded amino acids and peptidomimetics.

$X_1$ may be a carboxylic acid residue, e.g. acetyl, benzoyl or formyl group. $X_{12}$ may be an —OH or —$NH_2$ group. $X_1$ and $X_{12}$ may also be peptides. In yet another preferred embodiment of glyco-peptide I, R is selected from the group consisting of α-L or α-D-fucose and β-L or β-D-fucose.

In yet another preferred embodiment, the glycopeptide (I) is attached to a solid phase support.

In a most preferred embodiment, glyco-peptide (I) of the present invention is selected from the group consisting of:
Ac-Ser(α-L-Fuc)-Asp-Asp-$NH_2$,
Ac-Ser(α-L-Fuc)-Ser-Asp-$NH_2$,
Ac-Ser(α-L-Fuc)-Phe-Asp-$NH_2$,
Ac-Ser(α-L-Fuc)-Asn-Asp-$NH_2$,
Ac-Ser(α-L-Fuc)-Leu-Asp-$NH_2$,
Ac-Ser(α-L-Fuc)-Pro-Asp-$NH_2$,
Ac-Ser(β-L-Fuc)-Gly-Asp-$NH_2$,
Ac-Ser(β-L-Fuc)-Asp-Asp-$NH_2$,
Ac-Ser(β-L-Fuc)-Leu-Asp-$NH_2$,
Ac-Ser(β-L-Fuc)-Asn-Asp-$NH_2$,
Ac-Ser(α-L-Fuc)-Ala-Asp-$NH_2$,
Ac-Ser(β-L-Fuc)-Ala-Asp-$NH_2$,
Ac-Ser(β-L-Fuc)-Ser-Asp-$NH_2$,
Ac-Ser(β-L-Fuc)-Pro-Asp-$NH_2$,
Ac-Ser(α-L-Fuc)-Arg-Asp-OH,
Ac-Ser(α-L-Fuc)-Phe-Asp-OH,
Ac-Ser(α-L-Fuc)-Ser-Asp-OH,
Ac-Ser(α-L-Fuc)-Asn-Asp-OH,
Ac-Ser(α-L-Fuc)-Asp-Asp-OH,
Ac-Ser(α-L-Fuc)-Leu-Asp-OH,
Ac-Ser(α-L-Fuc)-Gly-Asp-OH,
Ac-Ser(α-L-Fuc)-Pro-Asp-OH,
Ac-Ser(β-L-Fuc)-Arg-Asp-OH,
Ac-Ser(β-L-Fuc)-Phe-Asp-OH,
Ac-Ser(β-L-Fuc)-Ser-Asp-OH,
Ac-Ser(β-L-Fuc)-Asn-Asp-OH,
Ac-Ser(β-L-Fuc)-Asp-Asp-OH,
Ac-Ser(β-L-Fuc)-Leu-Asp-OH,
Ac-Ser(β-L-Fuc)-Gly-Asp-OH,
Ac-Ser(β-L-Fuc)-Pro-Asp-OH,
Ac-Ser(α-L-Fuc)-Arg-Gly-OH,
Ac-Ser(α-L-Fuc)-Phe-Gly-OH,
Ac-Ser(α-L-Fuc)-Ser-Gly-OH,
Ac-Ser(α-L-Fuc)-Asn-Gly-OH,
Ac-Ser(α-L-Fuc)-Asp-Gly-OH,
Ac-Ser(α-L-Fuc)-Leu-Gly-OH,
Ac-Ser(α-L-Fuc)-Gly-Gly-OH,
Ac-Ser(α-L-Fuc)-Pro-Gly-OH,
Ac-Ser(β-L-Fuc)-Arg-Gly-OH,
Ac-Ser(β-L-Fuc)-Phe-Gly-OH,
Ac-Ser(β-L-Fuc)-Ser-Gly-OH,
Ac-Ser(β-L-Fuc)-Asn-Gly-OH,
Ac-Ser(β-L-Fuc)-Asp-Gly-OH,
Ac-Ser(β-L-Fuc)-Leu-Gly-OH,
Ac-Ser(β-L-Fuc)-Gly-Gly-OH,
Ac-Ser(β-L-Fuc)-Pro-Gly-OH,
Ac-Ser(α-L-Fuc)-Arg-Glu-$NH_2$,
Ac-Ser(α-L-Fuc)-Phe-Glu-$NH_2$,
Ac-Ser(α-L-Fuc)-Ser-Glu-$NH_2$,
Ac-Ser(α-L-Fuc)-Asn-Glu-$NH_2$,
Ac-Ser(α-L-Fuc)-Asp-Glu-$NH_2$,
Ac-Ser(α-L-Fuc)-Leu-Glu-$NH_2$,
Ac-Ser(α-L-Fuc)-Gly-Glu-$NH_2$,
Ac-Ser(α-L-Fuc)-Pro-Glu-$NH_2$,
Ac-Ser(β-L-Fuc)-Arg-Glu-$NH_2$,
Ac-Ser(β-L-Fuc)-Phe-Glu-$NH_2$,
Ac-Ser(β-L-Fuc)-Ser-Glu-$NH_2$,
Ac-Ser(β-L-Fuc)-Asn-Glu-$NH_2$,
Ac-Ser(β-L-Fuc)-Asp-Glu-$NH_2$,
Ac-Ser(β-L-Fuc)-Leu-Glu-$NH_2$,
Ac-Ser(β-L-Fuc)-Gly-Glu-$NH_2$, and
Ac-Ser(β-L-Fuc)-Pro-Glu-$NH_2$.

Another aspect of the current invention involves a method (Method 1) for identifying a glyco-peptide ligand for an acceptor molecule. Method 1 consists of the steps of:

(a) generating the glyco-peptide compound (I);

(b) introducing to glyco-peptide compound (I) an acceptor molecule of interest such that the acceptor molecule will recognize and bind to said glyco-peptide; and (c) isolating and defining a glyco-peptide that exhibits binding with the acceptor molecule.

In a preferred embodiment of Method 1, the acceptor molecule is selected from the group consisting of antibodies, lectins, receptors, viruses, bacteria, proteins, carbohydrates, nucleic acids, lipids, drugs, metals and small molecules.

In a most preferred embodiment of Method 1, the acceptor molecule is a selectin protein.

Another aspect of the current invention involves a method (Method 2) for identifying a biologically active glycopeptide ligand consisting of the steps of:

(a) generating glyco-peptide (I) which is attached to a solid phase support and in which the solid phase support is modified so that a portion of the glyco-peptide can be released;

(b) releasing a portion of the glyco-peptide from the solid phase support/glyco-peptide combination in situ;

(c) detecting the biological activity of the released glyco-peptide that exhibits the specific biological activity of interest;

(d) isolating a solid phase support/glyco-peptide combination that exhibits the specific biological activity of interest; and (e) determining the sequence of the glyco-peptide remaining in the solid phase support/glyco-peptide isolated in step (d).

In a preferred embodiment of Method 2 of the current invention, the solid phase support is modified to be acid-sensitive, base-sensitive, nucleophilic-sensitive, photosensitive, oxidation-sensitive, or reduction-sensitive.

In another preferred embodiment of Method 2 of the current invention, the in situ release of step (b) is affected by enzymatic cleavage, chemical cleavage or a photochemical cleavage.

In yet another preferred embodiment of Method 2 of the current invention the detection of step (c) is of a biological activity selected from the group consisting of cytotoxicity, anti-tumor activity, anti-bacterial activity, anti-fungal activity, anti-viral activity, anti-parasite activity, growth factor activity, growth inhibitor activity, hormone activity, neurotransmitter activity, immunomodulator activity, and anti-cell adhesion activity.

Another preferred embodiment of the instant invention concerns an anti-cell adhesion molecule, a therapeutic agent, a cytotoxic molecule, an anti-tumor molecule, an anti-microbial molecule, a growth factor agonist, a growth factor antagonist, a hormone agonist, a hormone antagonist, and a cytotoxic molecule consisting of a glyco-peptide sequence determined according to Methods 1 and 2 of the current invention. The present invention further provides therapeutic and diagnostic agents comprising glycopeptide sequences determined according to the foregoing methods.

The present invention provides for the identification of carbohydrate binding proteins or cellular adhesion inhibitors. Such inhibitors find use in numerous medical applications including use as anti-infectives, anti-inflammatories, contraceptives, etc.

DESCRIPTION OF THE FIGURES

FIG. 10A is an NMR spectrum of Ac-Ser(α-L-Fuc)-Gly-Asp-NH$_2$.

FIG. 10B is an NMR spectrum of Ac-Ser-Ser-Asp-NH$_2$.

DESCRIPTION OF THE PREFERRED EMBODIMENTS

Definitions

Figure 1:
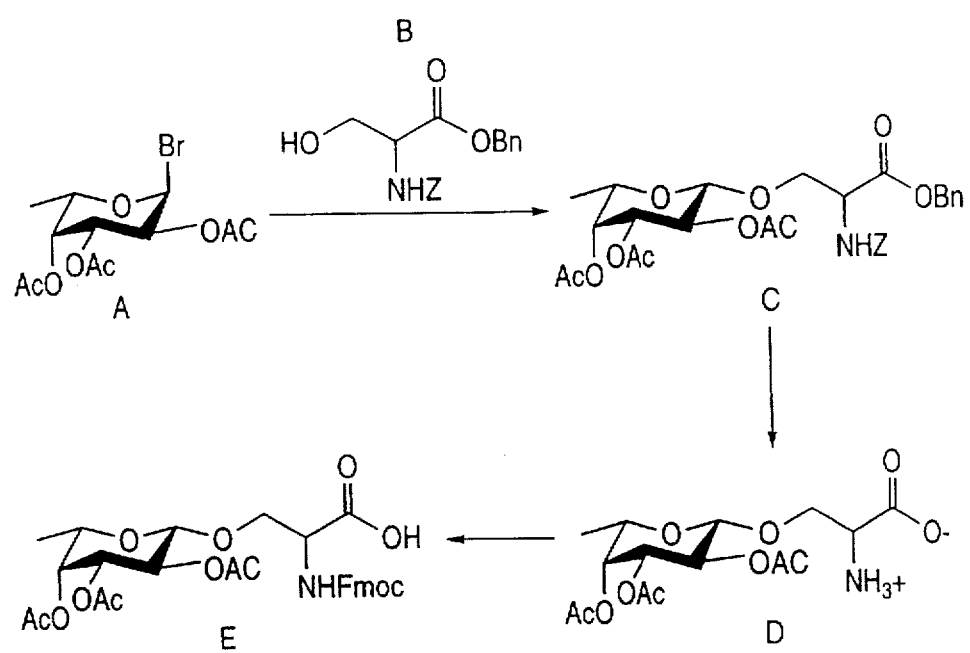
FIGS. 1A–1E show a diagram of the synthesis of Fmoc-Ser(Ac$_3$-β-L-Fuc).

The term "library" as used herein refers to a collection of bio-oligomers.

The term "bio-oligomer" refers to a polymer of less than about 100 subunits. A "bio-oligomer" of the instant invention may be a glyco-peptide; i.e., a chimera comprised of amino acid and carbohydrate subunits.

The term "lectin" as used herein refers to proteins that recognize specific carbohydrate residues and bind to cell surface glyco-proteins or glyco-lipids.

The term "peptidomimetic" as used herein refers to a molecule that structurally and chemically resembles a peptide of two or more amino acids The term "cell adhesion" as used herein refers to the initial contacts between two cells.

The term "selectin" as used herein refers to a family of cell surface receptors involved in the initial interactions between leukocytes and vascular endothelia leading to lymphocyte homing, platelet binding and neutrophil extravasation.

The term "fucose" as defined herein refers to compounds having the formula:

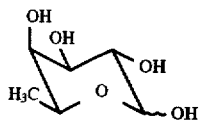

DETAILED DESCRIPTION OF THE INVENTION

Methods of Generating a Collection of Glyco-Peptides

Detailed methods of synthesis of the fucose-serine building blocks are provided in the example section below.

Fucose-serine building blocks are prepared using fluoren-9-yl-methoxycarbonyl (Fmoc) protection of amino groups, pentafluorophenol-ester (Pfp-ester) activation for coupling, triflouroacetic acid (TFA) sensitive side-chain protection and monitoring of coupling reactions calorimetrically using 3,4-dihydro-3-hydroxy-4-oxo-1,2,3-benzotriazine (Dhbt-OH) as an indicator.

Glyco-peptides are synthesized from the fucose-serine building blocks by activating with O-(benzotriazol-1-yl)-N, N,N',N'-tetramethyluroniumtetrafluoroborate (TBTU) and 4-ethylmorpholine, removing the Fmoc group with 20% piperidine or 50% morpholine in dimethylformamide (DMF), coupling the first amino acid as Dhbt ester to the linker, and introducing subsequent amino acids into the peptide chain as Dhbt-esters. The progress of the peptide bond formation is monitored by the decrease in coloration of the solid support. After attachment of the last amino acid and Fmoc removal, the terminal amino groups are acetylated with acetic anhydride in DMF. The glycopeptides are cleaved off the resin by treatment with 95% TFA with concurrent removal of the O-tBu groups. Deacetylation of the carbohydrate unit is performed with sodium methoxide in methanol or hydrazine in 50% methanol/water. Crude products are purified by preparative reverse phase HPLC. Compounds are characterized by 1D and 2D-1H-NMR.

A collection or library comprising glyco-peptides, oligonucleotides, or glyco-peptide-oligonucleotide chimeras may be generated by a method comprising repeating the step of:

(a) providing at least two aliquots of a solid phase support for the random subunit sequences;

(b) separately introducing a set of subunits to the aliquots of the solid phase support;

(c) completely coupling the subunits to substantially all of the sites of the solid phase support to form a solid phase support/new subunit combination;

(d) assessing the completeness of coupling and, if necessary, forcing the reaction to completeness;

(e) thoroughly mixing the aliquots of the solid phase support/new subunit combination;

and, after repeating steps (a)–(e) the desired number of times, a final step of (f) removing the protecting groups such that the bio-oligomer remains linked to the solid phase support.

Glyco-Peptide Libraries

In a particular embodiment, the bio-oligomer collection or library may comprise peptides. The term "peptide" is used in its broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. As used herein the term "amino acid" refers to either natural and/or unnatural or synthetic amino acids including glycine and both the D or L optical isomers, and amino acid analogs and peptidomimetics. A peptide of three or more amino acids is commonly called an oligopeptide if the peptide chain is short. If the peptide chain is long the peptide is commonly called a polypeptide or a protein.

The present invention is based on synthetic peptide chemistry and does not rely on any living system for amplification or screening. Peptide libraries can include unnatural amino acids. Thus, peptides of the invention may comprise D-amino acids, a combination of D- and L-amino acids, and various "designer" amino acids (e.g., β-methyl amino acids, $C^\alpha$-methyl amino acids, and $N^\alpha$-methyl amino acids, etc.) to convey special properties to peptides in the library. Additionally, by assigning specific amino acids at specific coupling steps, peptide libraries with α-helices, β turns, β sheets, γ-turns, and cyclic peptides can be generated.

The library of peptides of the invention includes all possible combinations of amino acids of which the peptides are composed. Using as an example a dipeptide made up of the two amino acids glycine and proline, there are four possible combinations: glycine-glycine, glycine-proline, proline-glycine, and proline-proline, and the random library will contain all four combinations.

A set of first amino acids is separately introduced to each aliquot. Generally, the amino acids used for peptide synthesis are the base-labile $N^\alpha$-amino protected 9-fluorenylmethoxycarbonyl (Fmoc) amino acids first described by Carpino and Han (1972, *J. Org. Chem.* 37:3403–3409). The method of the present invention may also be used with the Boc-amino acids ($N^\alpha$-amino protected $N^\alpha$-t-butyloxycarbonyl). Both Fmoc and Boc $N^\alpha$-amino protected amino acids can be obtained from Fluka, Bachem, Advanced Chemtech, Sigma, Cambridge Research Biochemical, Bachem, or Peninsula Labs or other chemical companies familiar to those who practice this art. In addition, the method of the invention can be used with other $N^\alpha$-protecting groups that are familiar to those skilled in this art.

Continuing with the dipeptide example described above, the first set of amino acids introduced would comprise glycine and proline; each aliquot receives either an $N^\alpha$-Fmoc-glycine or an $N^\alpha$-Fmoc-proline.

After introduction, the set of first amino acids is completely coupled to substantially all the sites of the solid phase supports. As used herein, complete coupling means that the coupling reaction is driven to completion irrespective of the differences in the coupling rates of individual amino acids. In addition, the amino acids are coupled to substantially all available coupling sites on the solid phase support so that each particle of the solid support will contain essentially only one species of peptide. Complete coupling will result in solid phase support/first amino acid combinations. Using the dipeptide described above as an example, the completion of the coupling will yield a bead-glycine combination and a bead-proline combination.

A spectrophotometric technique has been described for monitoring the course of acylation reactions in solid phase peptide synthesis using fluorenylmethoxycarbonyl amino acid 3,4-dihydro-4-oxo-1,2,3-benzotriazin-3-yl esters. The procedure has allowed construction of a fully automated peptide synthesizing system in which acylation and deprotection steps may be checked automatically for completion before proceeding to the next amino acid residue. (Cameron, et al., J. Chem. Soc. Perkin Trans. 1:2895–901 (1988))

In order to couple an amino acid to a growing synthetic chain, the carboxyl group of the blocked amino acid must be activated. Many methods of activation may be used in the practice of the invention and include for example, preformed symmetrical anhydrides (PSA), preformed mixed anhydride (PMA), acid chlorides, active esters, and in situ activation of the carboxylic acid, as set forth in Fields and Noble, 1990, and solid phase peptide synthesis utilizing 9-fluorenylmethoxycarbonyl amino acids, Int. J. Pept. Protein Res. 35:161–214.

The use of Fmoc amino acids is but one strategy of peptide synthesis. A Boc strategy (t-butyloxycarbonyl-protected a-amino group) may also be used to prepare a library of peptides bound to the solid phase support (e.g., Geysen et al., 1987, J. Immunol. Methods 102:259274.)

The completeness of coupling should be assessed. Those skilled in the art are familiar with the well known quantitative monitoring tests such as ninhydrin (the Kaiser test), picric acid, 2,4,6-trinitrobenzenesulfonic (TNBS), fluorescamine, and chloranil, which tests are based on reagent reaction with free amino groups to produce a chromophoric compound. If imino acids (e.g., Pro and Hyp) are used, isatin monitoring is a preferred method. Fields and Noble, supra. Quantification of reaction completeness may be monitored during the course of the reaction, e.g., as described by Salisbury et al. (International Patent Publication No. WO91/03485.

With Fmoc synthesis, the Kaiser test is preferred. In the Kaiser test, a sample from each tube can be tested with ninhydrin reagent obtained from Pierce Chemical in the method set forth by Sarin et al. (1981, Anal. Biochem. 117:147–157.

If the coupling reaction is incomplete as determined by this test, the reaction can be forced to completion by several methods familiar to those in the art, including (a) a second coupling using a one to five fold excess of protected amino acid, (b) an additional coupling using different or additional solvents (e.g., trifluoroethane), or (c) the addition of chaotropic salts, e. g., NaClO$_4$ or LiBr (Klis and Stewart, 1990, Peptides: Chemistry, Structure and Biology, Rivier and Marshall, eds., ESCOM Publ., p. 904–906.

After the coupling reaction is complete the aliquots of the solid phase support/first amino acid combinations are thoroughly mixed. Thorough mixing is obtained when a uniform mixture of the aliquots results, preferably by mixing the aliquots in a single reaction vessel. Although any means of thorough mixing is within the scope of this invention and a variety of means are familiar to those of ordinary skill in the art, preferable means may include, for example, vortexing or shaking in any commercially available motorized shaker apparatus or by bubbling with inert gas, e.g., nitrogen or argon.

The resulting mixture is divided into at least two aliquot parts. These aliquot parts are equal in volume and, if the mixing was sufficiently thorough, should contain substantially equal amounts of the solid phase support/first amino acid combinations. Using the dipeptide example, each aliquot will contain essentially equal amounts of the bead-glycine combination and the bead-proline combination.

To each aliquot is separately introduced a second set of amino acids. This second set may consist of (a) the same amino acids added in the first set, i.e., glycine or proline; (b) a different set of amino acids, e.g., tryptophan or leucine; (c) only one type of amino acid, e.g., isoleucine.

As with the first set of amino acids, the second set of amino acids is completely coupled individually to the solid phase support/first amino acid combination of each aliquot to form peptides comprising a first amino acid and a second amino acid. As with the prior coupling, the coupling may be accomplished by any technique used in the art for such reactions. Using the dipeptide example discussed above: (a) with the addition of the same set of amino acids, the resulting peptides are either glycine-glycine, glycine-proline, proline-glycine, or proline-proline; (b) with a different set of amino acids, the resulting peptides are either Gly-Trp, Gly-Leu, Pro-Trp or Pro-Leu; (c) with one type of amino acid, the resulting peptides are Gly-Ile or Pro-Ile.

This method can be repeated as many times as there are amino acids to add. If the peptide of interest is a tetrapeptide X-X-X-Trp, where X is either valine, serine or alanine, for example, the method can be repeated three times to get the X-X-X-Trp tetrapeptide. If a hexapeptide is desired, the process is repeated six times. If the hexapeptide is to be comprised of five different amino acids, the method could be employed using five aliquots, each containing a different amino acid, at each coupling step. If, however, the hexapeptide is to be comprised of any of the basic set of twenty amino acids, the method could be employed using twenty aliquots at each coupling step.

The method of the peptide synthesis of the invention can be used with solid phase supports to which an amino acid either is or is not already attached. In addition, one may use a linker that has already been attached to the solid phase support. One common support to which an amino acid is already bound is the -alanine-PAM-resin (obtained from Bachem Biochemical). These resins are available from numerous commercial sources or made in the laboratory by one knowledgeable in the art of peptide synthesis.

If a solid phase support/amino acid combination or solid phase/support linker is used as the initial reagent, it is divided into at least two aliquots, each of which receives an amino acid from a first set of amino acids. As described above, the first set of amino acids is completely coupled to substantially all binding sites on the solid phase support/ amino acid combination or solid phase support/linker and the aliquots containing these newly added amino acids are thoroughly mixed. As described above, the mixture is divided into at least two aliquots, each aliquot receives an amino acid from a second set of amino acids, and the coupling reaction is repeated to form a growing peptide. As described above, the process can be repeated as many times as is desired to produce the peptides of interest.

This method may be used for the synthesis of random peptides as well as for the synthesis of a peptide library that comprises pre-determined sequences. The synthesis of pre-determined sequences involves the use of specific $N^\alpha$-Boc-, $N^\alpha$-Fmoc- or other appropriately protected amino acids during specific coupling steps. For example, one may select amino acids at specific coupling steps such that the resulting peptides will have a probability or preference for a particular secondary structure, e.g., β-sheet, α-helix, β-turn, etc. For example, α-helix would be preferred if Glu, Ala, Leu, His, Trp are used as preferred amino acids; on the other hand β-sheets would be preferred if Val, Ile, Tyr and Met are used. Alternatively, if Gly, Asn, Ser, Pro, Asp are used, a β-turn structure would be preferred. Other examples could be considered such as acidic amino acids near the N-terminal, and basic amino acids near the C-terminal, to stabilize an α-helix. D-amino acids can stabilize certain turns, and numerous other structural motifs can be incorporated. It may even be possible to prepare cyclic peptide libraries with disulfide, lactam, lactone or other ring closing moieties.

It is to be emphasized that the method of the instant invention allows the synthesis of peptides such that each solid phase support, such as a resin bead, will contain only one species of peptide. The method assures that each individual resin bead is in contact with only one Fmoc amino acid during each coupling cycle and that the coupling is driven to completion. The one bead-one peptide synthesis allows increased sensitivity and efficiency of isolating the peptide that is specific for the entity to which it binds.

The use of $N^\alpha$-Fmoc-Ser(Ac$_3$-α-D-GalpNAc-OPfp) and $N^\alpha$-Fmoc-Thr(Ac$_3$-α-D-GalpNAc)-OPfp and their application in multiple-column solid-phase synthesis of O-glycopeptides is well known in the art. (Peters et al. (1992) 1:1163–1171). The protecting group pattern of these building blocks is suitable for solid-phase glycopeptide synthesis. The use of Fmoc allows deprotection of the α-amino group under mild conditions with morpholine to occur without β-elimination of the carbohydrate.

In one aspect of the invention, the library of peptides comprises at least 3 amino acids. In another embodiment, the amino terminal amino acid is a serine to which a carbohydrate is o-glucosidically linked. In yet another embodiment, the amino terminal peptide is N-acetylated. In a further embodiment, the penultimate amino acid is a serine to which a carbohydrate is o-glucosidically linked. In yet a further embodiment, the carbohydrate is a fucose moiety.

Solid Phase Supports and Linkers for Use in a Glyco-Peptide Library

A solid phase support for use in the present invention will be inert to the reaction conditions for bio-oligomer synthesis, e.g., peptide synthesis or oligonucleotide synthesis, or both. A solid phase support for use in the present invention must have reactive groups in order to attach a monomer subunit, or for attaching a linker or handle which can serve as the initial binding point for a monomer subunit. In one embodiment, the solid phase support may be suitable for use, i.e., it may serve as a carrier for or support for direct applications of the bio-oligomer library (e.g., TentaGel, Rapp Polymere, Tubingen, Germany; see Section 5.8., infra). In a particular embodiment, the solid phase support may be palatable and orally consumable. In another embodiment, the solid phase support may be a useful chromatographic support.

As used herein, solid phase support is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from Milligen/Biosearch, California). In a preferred embodiment for peptide synthesis, solid phase support refers to PEGA resin (BACHEM) as described in Meldal, et al., Tetrahedron Lett. 33:3077–3080 (1992).

The solid phase supports of the invention may also comprise a linker. As used herein, a linker refers to any molecule that provides spatial distance between the support and the peptide to be synthesized. Linkers can be covalently attached on the solid phase support prior to coupling with a $N^\alpha$-Boc or $N^\alpha$-Fmoc or otherwise appropriately protected amino acids. Various linkers can be used to attach the oligomer to solid phase support. Examples of linkers include aminobutyric acid, aminocaproic acid, 7-aminoheptanoic acid, and 8-aminocaprylic acid. Fmoc-aminocaproic acid is commercially available from Bachem Biochem, and is the preferred embodiment. In a further embodiment, linkers can additionally comprise one or more β-alanines as spacers. In addition, the solid-support could be modified to meet specific requirements for the particular purpose of bioassay or detection. Modification of solid phase support may be made by incorporation of a specific linker. For example, modified solid phase support could be made acid-sensitive, base-sensitive, nucleophilic electrophilic sensitive, photosensitive oxidation sensitive or reduction sensitive.

In addition to the linkers described above, selectively cleavable linkers may be employed. Use of an ultraviolet light sensitive linker, ONb, is shown in Section 12, infra (see Sarany and Albenicia, 1985, *J. Am. Chem. Soc.* 107:4936–4942). Other cleavable linkers require hydrogenolysis or photolysis. Examples of photosensitive (photocleavable) linkers are found in Wang (1976, *J. Org. Chem. Soc.* 41:32–58), Hammer et al. (1990, *Int. J. Pept. Protein Research* 36:31–45), and Ereib-Cordonier et al. (1990, in *Peptides-Chemistry and Biology* Rivier and Marshall, eds., pp. 895–897). Landen (1977, *Methods Enzymology.* 47:145–149) used aqueous formic acid to cleave Asp-Pro bonds; this approach has been used to characterize T-cell determinants in conjunction with the Geysen pin synthesis method (Van der Zee et al., 1989, *Eur. J. Immunol.* 191:43–47). Other potential linker groups cleavable under basic conditions include those based on p-(hydroxylmethyl) benzoic acid (Atherton et al., 1981, *J. Chem. Soc.* 1:538–546) and hydroxyacetic acid (Baleaux et al., 1986, *Int. Pept. Protein Res.* 28:22–28). Geysen et al. (1990, *J. Immunol. Methods* 134:23–33) reported peptide cleavage by a diketopiperazine mechanism. An enzyme may specifically cleave a linker that comprises a sequence that is sensitive or a substrate for enzyme cleavage, e.g., protease cleavage of a peptide; endonuclease cleavage of an oligonucleotide. In certain instances, one may derivatize 10–50% of the resin by substitution with the cleavable linker, and the remaining 50–90% substituted with a noncleavable linker to ensure that enough peptide will remain after cleavage of linker be left behind for sequencing.

A solid phase support for use in the present invention may further comprise a bio-oligomer of interest, to which a random subunit sequence may be added. The pre-attached bio-oligomer may be selected according to the methods described herein, or may comprise a sequence known to embody desired properties.

Methods of Detection and Identification of Bio-Oligomer Glyco-Peptides of Interest In addition to providing a collection of bio-oligomer glyco-peptides or a library and methods of synthesis thereof, the present invention further comprises methods of screening a collection of or library of bio-oligomer glyco-peptides to identify bio-oligomers within the collection or library that demonstrate a biological activity of interest.

The present invention allows identification of bio-oligomer ligands that bind acceptor molecules. As used-herein, the term "acceptor molecule" refers to any substance which binds to a bio-oligomer ligand. Acceptor molecules may be a biologic macromolecule such as, but not limited to, lectins, antibodies, receptors, viruses or selecting. In addition, acceptor molecules may be a chemical compound such as, but not limited to, proteins, carbohydrates, nucleic acids, lipids, drugs, metals or small molecules.

The collection of or library of bio-oligomer glyco-peptides of the invention can potentially interact with many different acceptor molecules. By identifying the particular bio-oligomer species to which a specific acceptor molecule binds, it is possible to physically isolate the bio-oligomer species of interest.

Because only a small number of bio-oligomers will be removed during each screening/detection/isolation step, the majority of the beads will remain in the pool. Therefore, the bio-oligomer glyco-peptide library can be reused multiple times. If different color or identification schemes are used for different acceptor molecules (e g., with fluorescent reporting groups such as fluorescein (green), Texas Red (Red) and DAPI (blue) tagged on the acceptors), and with suitable excitation filters in the fluorescence microscope or the fluorescence detector, different acceptors (receptors) can be added to a peptide library and evaluated simultaneously to facilitate rapid screening for specific ligands. These strategies not only reduce cost, but also increase the number of acceptor molecules that can be screened.

In the method of the invention, an acceptor molecule of interest is introduced to the collection of or library of bio-oligomers where it will recognize and bind to one or more bio-oligomer species within the library. Each bio-oligomer species to which the acceptor molecule binds will be found on a single solid phase support so that the support, and thus the bio-oligomer, can be readily identified and isolated.

The bio-oligomer can be isolated by any conventional means known to those of ordinary skill in the art and the invention is not limited by the method of isolation. For example and not by way of limitation, it is possible to physically isolate a solid phase support/bio-oligomer combination that exhibits the strongest physio-chemical interaction with the specific acceptor molecule. In one embodiment based on physio-chemical interaction, a solution of a specific acceptor molecule is added to a random peptide library which is equivalent to approximately $10^5$ to $10^7$ solid phase supports. The acceptor molecule is incubated with the resin for a time sufficient to allow coupling between the peptide and antibody, for example, one hour at 22° C. Thereafter, the acceptor molecule coated bio-oligomer/solid phase support is isolated. More specific embodiments are set forth in the following methods.

The invention having been described, the following examples are offered to illustrate the subject invention by way of illustration, not by way of limitation.

EXAMPLES

I. Synthesis and characterization of Fmoc-Ser($\beta$-Fuc(Ac$_3$)). (FIGS. 1A–1E)

N-Carboxybenzoyloxy-3-O-(2,3,4-tri-O-acetyl-$\beta$-L-fucopyranosyl)-L-serine Benzyl Ester (FIG. 1C)

To a solution of commercial N-(carboxybenzoyloxy)-3-O-(2,3,4-tri-O-benzyl-a-L-fucopyranosyl)-L-serine benzyl ester (Bachem, 2.17 gm, 6.61 mmol) in dry acetonitrile (17 ml) containing powdered drierite (1.6 gm) were added, sequentially under nitrogen atmosphere, mercuric bromide (2.86 gm, 7.93 mmol), mercuric cyanide (2.00 gm, 7.93 mmol) and a solution of acetobromofucose (2.33 gm, 6.61 mmol) in dry acetonitrile (10 ml). The reaction mixture was stirred for 15 h at room temperature and then filtered through celite. Evaporation of the solvent gave a residue, which was extracted with dichloromethane and washed successively with saturated aqueous potassium chloride, saturated aqueous sodium bicarbonate and water. The organic layer was dried, filtered, and evaporated to dryness. The while solid was purified by chromatography on silica gel using hexane-ethyl acetate 2:1 as eluent. Pure N-Carboxybenzoyloxy-3-O-(2,3,4-tri-O-acetyl-$\beta$-L-fucopyranosyl)-L-serine Benzyl Ester (2.1 gm, 52.9%) was obtained as a white solid. $R_f$=0.38 (hexane:ethyl acetate 2:1, developed 3 times). $^1$H-NMR (CDCl$_3$): $\epsilon$ 7.45-7.30 (10 H, aromatic), 5.75 (d, 1 H, $J_{NH,2}$=9.0 Hz, NH), 5.26 (d, 1 H, $J_{gem}$=12 Hz, PhCH), 5.18 (dd, 1 H, $J_{3,4}$=3.0, $J_{4,5}$=1.0 Hz, H-4), 5.13-5.07 (m, 4 H, 3×PhCH and H-2), 4.91 (dd, 1 H, $J_{2,3}$=10.5 Hz, H-3), 4.54 (ddd, J=3.0, 3.0, 9.0 Hz), serine CHN), 4.21 (d, 1 H, J=8.0 Hz, H-1), 4.06 (m, 2 H, serine CH$_2$), 3.64 (dq, $J_{5,6}$=6.5 Hz, H-5), 2.16, 2.00 and 1.97 (each s, 3 H, Ac), 1.17 (d, 3 H, H-6). 3-O-(2,3,4-tri-O-acetyl-$\beta$-L-fucopyranosyl)-L-serine (FIG. 1D).

A solution of N-Carboxybenzoyloxy-3-O-(2,3,4-tri-O-acetyl-$\beta$-L-fucopyranosyl)-L-serine Benzyl Ester (600 mg, 1.0 mmol) in 98% ethanol (15 ml) containing 5% Pd/C (300 mg) was hydrogenated for 16 h at room temperature and at 1 atmospheric pressure. The catalyst was collected on celite and washed with several portions of 98% ethanol. The filtrate and washings were combined and concentrated to dryness to give 3-O-(2,3,4-tri-O-acetyl-$\beta$-L-fucopyranosyl)-L-serine (306.6 mg, 81.6%) as a white powder $R_f$=0.34 (dichloromethane:methanol:water, 60:35:3). $^1$H-NMR (CD$_3$OD): $\epsilon$ 5.23 (dd, 1 H, $J_{3,4}$=3.0, $J_{4,5}$=1.0 Hz, H-4), 5.14-5.02 (m, 2 H, H-2 and 3), 4.68 (d, 1 H, $J_{1,2}$=7.5 Hz, H-1), 4.24 (dd, 1 H, $J_{gem}$=7.5 Hz, H-1), 4.24 (dd, 1 H, $J_{gem}$=10.5, $J_{CH,CHN}$=2.0 Hz, serine CH), 4.13-4.04 (m, 2 H, serine CHH and CHN), 4.01 (dq, $J_{5,6}$=6.5 Hz, H-5), 2.13, 2.05 and 1.93 (each s, 3 H, Ac), 1.19 (d, 3 H, H-6). N-(9-Fluorenylmethyloxycarbonyl)-3-O-(2,3,4-tri-O-acetyl-$\beta$-L-fucopyranosyl)-L-serine (FIG. 1E).

A solution of 3-O-(2,3,4-tri-O-acetyl-$\beta$-L-fucopyranosyl)-L-serine (FIG. 1D) (209.6 mg, 0.82 mmol) and Fmoc N-hydroxysuccinimide ester (9-fluorenylmethyl-N-succinimidyl carbonate) (375.7 mg, 1.63 mmol) in dry pyridine (25 ml) was stirred for 15 h at room temperature. Evaporation and co-evaporation of the reaction mixture with toluene left a syrup which was purified by chromatography on silica gel using dichloromethane-methanol 95:5 as eluent. Pure N-(9-Fluorenylmethyloxycarbonyl)-3-O-(2,3,4-tri-O-acetyl-$\beta$-L-fucopyrano syl)-L-serine (294 mg, 88%) was obtained as a white powder, $R_f$=0.40 (9:1, dichloromethane:methanol). $^1$H-NMR (CD$_3$OD): $\epsilon$ 7.82-7.25 (m, 8 H, aromatic), 5.18 (m, 1 H, sec. order, H-4), 5.08-4.98 (m, 2 H, sec. order, H-2, 3), 4.50 (d, 1 H, $J_{1,2}$=7.5 Hz, H-1), 4.44-3.95 (complex, 6 H, Fmoc-H and serine H's), 3.83 (q, $J_{5,6}$=6.25 Hz, H-6), 2.11, 1.99 and 1.92 (each s, 3 H, Ac), 1.10 (d, 3 H, H-6). $^{13}$C: ε 102.6 (C-1), 72.5, 71.8 and 70.3 (C-2, 3 and 4), 71.5 and 67.9 (FMOC and serine CH$_2$), 56.5 (serine CHN), 20.8, 20.5 and 20.4 (COCH$_3$), 16.3 (C-6).

II. Synthesis and characterization of Fmoc-Ser (α-Fuc(Ac$_3$)) (FIGS. 2A–2F)

Figure 2:
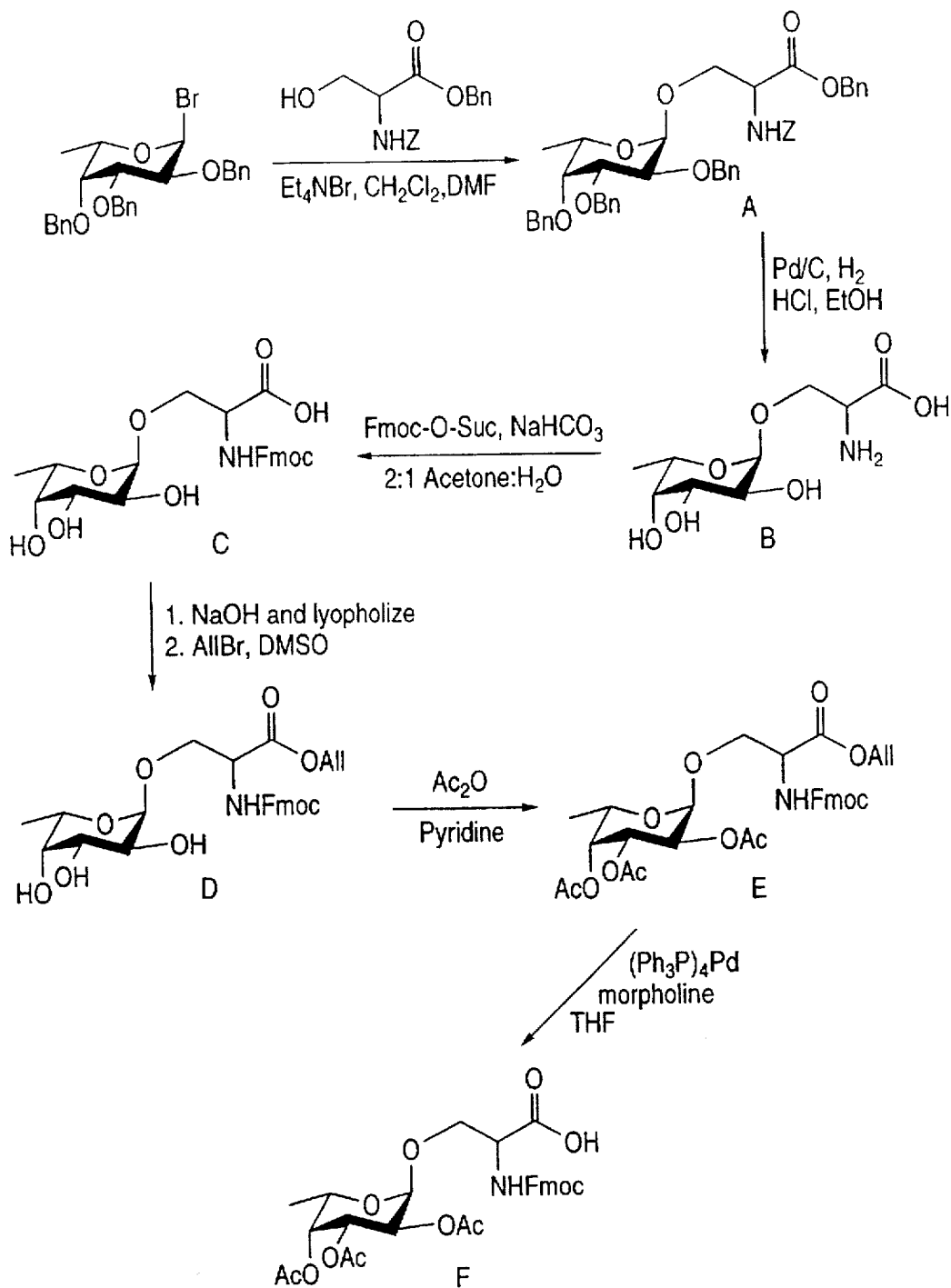
FIGS. 2A–2F show a diagram of the synthesis of Fmoc-Ser(Ac$_3$-α-L-Fuc).

N-(carboxybenzoyloxy)-3-O-(2,3,4-tri-O-benzyl-a-L-fucopyranosyl)-L-serine benzyl ester. (FIG. 2-A). N-carboxybenzoyloxy-L-serine benzyl ester (dried under vacuum overnight with phosphorus pentoxide, 5.04 g, 15.3 mmol) and tetraethylammonium bromide (3.47 g, 16.83 mmol) were dissolved in dichloromethane (30 mL) and dimethylformamide (2 mL) containing crushed 4A molecular sieves (15 g). The solution was stirred under argon for thirty minutes. To this slurry was added freshly prepared 2,3,4-tri-O-benzyl-fucopyranosyl bromide (U. Spohr and R. U. Lemieux, Carbohydr. Res., 174 (1988) 211), (38.3 mmol) in dichloromethane (20 mL) and the reaction allowed to stir for 15 hours under argon. Methanol (10 mL) was added and stirring continued for thirty minutes after which the reaction was filtered, diluted with dichloromethane, and washed with water and brine. After drying and solvent removal, the residue was chromatographed (3:1 hexane:ethyl acetate) to give N-(carboxybenzoyloxy)-3-O-(2,3,4-tri-O-benzyl-a-L-fucopyranosyl)-L-serine benzyl ester (9.49 g, 85%) as an oil which solidified upon standing. [a]$_D$-57.7 (c=0.91, chloroform). R$_f$=0.30 (3:1 hexane:ethyl acetate). $^1$H-NMR (CDCl$_3$): ε 7.10–7.15 (m, 25 H, Ph), 6.09 (d, 1 H, J$_{NH,CH}$= 9.5 Hz, NH), 5.23 (d, 1 H, J$_{gem}$=11.5 Hz, PhCH$_2$), 5.13 (s, 2 H, PhCH$_2$), 5.05, 4.92, 4.76, 4.77 (d, 1 H, J$_{gem}$=11.5 Hz, PhCH$_2$), 4.52–4.69 (m, 5 H, 3 PhCH$_2$, serine CHNH, H-1), 4.16 (dd, 1 H, J$_{gem}$=10 Hz, J$_{vic}$=2.5 Hz, serine CH$_2$), 3.94 (dd, 1 H, J$_{1,2}$=4 Hz, J$_{2,3}$=10 Hz, H-2), 3.60 (dd, 1H, J$_{2,3}$=10 Hz, J$_{3,4}$=2.5 Hz, H-3), 3.48 (d, 1 H, J$_{gem}$=10 Hz, J$_{vic}$=3.5 Hz, serine CH$_2$), 3.29–3.40 (m, 2 H, H-4, H-5), 0.91 (d, 3H, J$_{5,6}$=6.5 Hz). $^{13}$C-NMR: ε170.10 (C=O ester), 156.30 (C=O), carbamate), 138.88, 138.53, 136.35, 135.51 (Ph quat.), 128.62, 128.57, 128.50, 128.38, 128.19, 128.14, 127.83, 127.64, 127.54 (Ph methine) 98.87 (C-1), 78.87 (C-4), 77.36 (C-3), 76.50 (C-2), 74.74, 73.31, 73.23 (PhCH$_2$), 69.03 (serine CH$_2$), 67.15, 67.07 (PhCH$_2$), 66.68 (C-5), 54.51 (serine CHNH), 16.48 (C-6).

Anal. Calc. for C$_{44}$H$_{47}$NO$_9$ (733.86): C, 72.01; H, 6.46; N, 1.91. Found: C, 72.34; H, 6.45; N, 1.93.

3-O-(α-L-fucopyranosyl)-L-serine. (FIG. 2B). The protected glycoamino acid A (6.5 g, 8.86 mmol) was dissolved in ethanol (75 mL) and water (20 mL). 2N HCl (4.5 mL) and 10% palladium on carbon (2.5 g) were added and the solution stirred under a flow of hydrogen for 24 hours. After completion of the reaction, the catalyst was filtered away and the solvent evaporated to give 3-O-(α-L-fucopyranosyl)-L-serine in quantitative yield (2.22 g) as a white solid. $^1$H-NMR (D$_2$O): 4.90 (d, 1 H, J$_{1,2}$=3.5 Hz, H-1), 4.20–4.29 (m, 2 H, serine CH$_2$, serine CHNH), 3.93 (q, 1 H, J$_{5,6}$=6.5 Hz, H-5), 3.75–3.85 (m, 4 H, serine CH$_2$, H-2, H-3, H-4), 1.19 (d, 3H, J$_{5,6}$=6.5 Hz, H-6). $^{13}$C-NMR: ε 171.39 (C=O), 98.83 (C-1), 72.48 (C-4), 70.28 (C-3), 68.77 (C-2), 68.01 (C-5), 65.71 (serine CH$_2$), 54.37 (serine CHNH$_2$), 16.01 (C-6). N-(9-Fluorenylmethyloxycarbonyl)-3-O-(α-L-fucopyranosyl)-L-serine. (FIG. 2C). 3-O-(α-L-fucopyranosyl)-L-serine (2.22 g, 8.86 mmol) was dissolved in acetone (100 mL) and water (50 mL). Sodium bicarbonate (745 mg, 8.86 mmol) and 9-fluorenylmethyl-N-succinimidyl carbonate (6.0 g, 17.8 mmol) was added and the solution stirred overnight. The reaction was extracted with ethyl acetate, the pH of the aqueous layer brought to 9 by the addition of sodium hydroxide and the aqueous layer lyophilized to give N-(9-Fluorenylmethyloxycarbonyl)-3-O-(α-L-fucopyranosyl)-L-serine. R$_f$=0.21 (2:1 dichloromethane:methanol) which was not further purified. $^1$H-NMR (CD$_3$OD): 7.15–7.70 (m, 8H, Fmoc aromatic), 4.64 (d, 1H, J$_{1,2}$=3.5 Hz, H-1), 4.21–4.33 (m, 3 H, 2 Fmoc CH$_2$, serine CHNH), 4.06–4.15 (m, 2H, serine CH$_2$, Fmoc CH), 3.80 (q, 1 H, J$_{5,6}$=6.5 Hz, H-5), 3.65 (dd, 1 H, J$_{1,2}$=3.5 Hz, J$_{2,3}$=9.5 Hz, H-2), 3.56 (dd, 1 H, J$_{2,3}$=9.5 Hz, J$_{3,4}$=2.5 Hz, H-3), 3.50 (d, J$_{3,4}$=2.5 Hz, H-4), 3.46 (dd, 1 H, J$_{gem}$=9.5 Hz, J$_{vic}$=1 Hz, serine CH$_2$), 1.08 (d, 3 H, J$_{5,6}$=6.5 Hz, H-6). N-(9-Fluorenylmethyloxycarbonyl)-3-O-(α-L-fucopyranosyl)-L-serine allyl ester. (FIG. 2D). N-(9-Fluorenylmethyloxycarbonyl)-3-O-(α-L-fucopyranosyl)-L-serine was dissolved in dimethylsulfoxide (100 mL) and allyl bromide (25 mL) added. After stirring for 4 hours, the reaction was diluted with ethyl acetate and washed with water and brine. The organic layer was evaporated to dryness and the residue chromatographed (9:1 dichloromethane:methanol) to give N-(9-Fluorenylmethyloxycarbonyl)-3-O-(α-L-fucopyranosyl)-L-serine allyl ester (2.32 g, 51% from 3-O-(α-L-fucopyranosyl)-L-serine) as a yellow foam. R$_f$=0.51 (9:1 dichloromethane:methanol). $^1$H-NMR (CD$_3$OD): 7.28–7.81 (m, 8 H, Fmoc aromatic), 5.93 (1 H, H$_c$ allyl), 5.37 (1 H, H$_a$ allyl), 5.27 (1 H, H$_b$ allyl), 4.80 (d, J$_{1,2}$=3.5 Hz, H-1), 4.62–4.71 (m, 2 H, H$_d$ and H$_e$ allyl), 4.59 (t, J$_{vic}$- 2.5 Hz, CHNH), 4.47, 4.38 (dd, 1 H, J$_{gem}$=10 Hz, J$_{vic}$=7 Hz, Fmoc CH$_2$), 4.22–4.32 (m, 2 H, H-2, H-3), 3.72–3.82 (m, 2 H, Fmoc CH, H-5), 3.61–3.68 (m, 2 H, H-4, serine CH$_2$), 3.58 (dd, 1 H, J$_{gem}$=9 Hz, J$_{vic}$=2.5 Hz, serine CH$_2$), 1.23 (d, 3 H, J$_{5,6}$=6.5 Hz, H-6). N-(9-Fluorenylmethyloxycarbonyl)-3-O-(2,3,4-tri-O-acetyl-a-L-fucopyrano syl)-L-serine allyl ester. (FIG. 2E). To a solution of N-(9-Fluorenylmethyloxycarbonyl)-3-O-(α-L-fucopyranosyl)-L-serine allyl ester (3.68 g, 7.18 mmol) in dichloromethane (75 mL) was added pyridine (7 mL, 86.15 mmol) and acetic anhydride (8.15 mL, 86.15 mmol). After stirring overnight, the reaction was diluted with dichloromethane then washed with water, bicarbonate and brine. The organic layer was evaporated to dryness and the residue chromatographed (2:1 ethyl acetate:hexane) to give N-(9-Fluorenylmethyloxycarbonyl)-3-O-(2,3,4-tri-O-acetyl-a-L-fucopyrano syl)-L-serine allyl ester (3.97 g, 87%) as a white foam. [a]$_D$- 77.0 (c=1.65, chloroform), R$_f$=0.60 (1:1 hexane:ethyl acetate). $^1$H-NMR (CDCl$_3$): 7.28–7.80 (m, 8 H, Fmoc aromatic), 5.96 (1 H, H$_c$allyl), 5.59 (d, 1 H, J$_{NH,CH}$= 8.5 Hz, NH), 5.38 (1 H, H$_a$ allyl), 5.28 (1 H, H$_b$ allyl), 5.18–5.28 (m, 2 H, H-3, H-4), 5.13 (d, 1 H, J$_{1,2}$=3.5 Hz, H-1), 5.03–5.11 (m, 1 H, H-2), 4.63–4.79 (m, 2H, H$_d$ and H$_e$ allyl), 4.60 (ddd, J$_{CH,NH}$=8.5 Hz, J$_{vic}$=2.5 Hz, J$_{vic}$=3.0 Hz, CHNH), 4.49, 4.39 (dd, 1 H, J$_{vic}$=7 Hz, J$_{gem}$=10.5 Hz, Fmoc CH$_2$), 4.23 (t, 1 H, J$_{vic}$=7 Hz, Fmoc CH) 4.20 (dd, 1 H, J$_{vic}$=2.5 Hz, J$_{jem}$=10.5 Hz, serine CH$_2$), 4.03 (q, 1 H, J$_{5,6}$=6.5 Hz, H-5), 3.68 (dd, 1 H, J$_{vic}$=3.0 Hz, J$_{gem}$=10.5 Hz, serine CH$_2$), 2.17, 2.02, 1.98 (s, 3 H, acetate CH$_3$), 1.10 (d, 3 H, J$_{5,6}$=6.5 Hz,H-6). $^{13}$C-NMR: ε 170.54, 170.38, 169.96, 169.41 (C=O ester), 155.87 (C=O carbamate), 143.83, 143.66, 141.33 (Ph quaternary), 131.37 (CH$_2$=CHCH$_2$O), 127.77, 127.11, 125.03, 120.03 (Ph methine), 119.47 (CH$_2$=CHCH$_2$O), 96.84 (C-1), 70.89 (C-4), 68.51 (CH$_2$=CHCH$_2$O), 68.02 (C-3), 67.95 (C-2), 67.19 (Fmoc CH$_2$), 66.52 (serine CH$_2$), 64.83 (C-5), 54.31 (serine CHNH), 47.16 (Fmoc CH), 20.69, 20.62 (acetate CH$_3$), 15.83 (C-6).

Anal. Calc. for C$_{33}$H$_{37}$NO$_{12}$(639.66): C, 61.97; H, 5.83; N, 2.19. Found: C, 62.02; H, 5.75; N, 2.21. N-(9-Fluorenylmethyloxycarbonyl)-3-O-(2,3,4,-tri-O-acetyl-a-L- fucopyranosyl)-L-serine. (FIG. 2F). N-(9-Fluorenylmethyloxycarbonyl)-3-O-(2,3,4-tri-O-acetyl-a-L-fucopyrano syl)-L-serine allyl ester (3.70 g, 5.79 mmol) was dissolved in tetrahydrofuran (75 mL) and then morpholine (1 mL, 11.58 mmol) and tetrakis triphenylphosphine palladium (670 mg, 0.579 mmol) were added. After stirring for five minutes, the reaction was diluted with dichloromethane then washed with 0.5N hydrochloric acid, water and brine. The organic layer was evaporated to dryness and the residue chromatographed (9:1 dichloromethane:methanol) to give N-(9-Fluorenylmethylosycarbonyl)-3-O-(2,3,4,-tri-O-acetyl-a-L-fucopyrano syl)-L-serine (3.11 g, 90%) as a white foam, $F_f$=0.43 (9:1 dichloromethane:methanol). $^1$H-NMR (CD$_3$OD); 7.16–7.73 (m, 8H Fmoc aromatic) 5.06–5.23 (m, 2H, H-3, H-4), 4.88–4.98 (m, 2H, H-1, H-2), 4.35, 4.28 (dd, 1 H, $J_{gem}$=10 Hz, $J_{vic}$=6.5 Hz, Fmoc CH$_2$), 4.02–4.18 (m, 3H, H-5, Fmoc CH, serine CHNH), 3.91 (dd, 1 H, $J_{gem}$=9.5 Hz, $J_{vic}$=9.5 Hz, $J_{vic}$=5.5 Hz, serine CH$_2$), 3.68 (dd, 1 H, $J_{gem}$=9.5 Hz, $J_{vic}$=3.0 Hz, serine CH), 2.04 (s, 3 H acetate CH$_3$), 1.86 (s, 6 H, 2 acetate CH$_3$), 0.95 (d, 3 H, $J_{5,6}$=6.5 Hz, H-6). $^{13}$C-NMR: ε 172.29, 171.98, 171.64 (C=O, ester), 158.34 (C=O, carbamate), 145.33, 145.23, 142.57 (Ph quaternary), 128.76, 128.22, 126.11, 120.93 (Ph methine), 97.33 (C-1), 72.51 (C-4),69.55 (C-3), 69.38 (C-2), 67.89 (Fmoc CH$_2$, serine cH$_2$), 65.81 (C-5), 56.85 (serine CHNH), 48.35 (Fmoc CH), 20.71, 20.63, 20.45 (acetate CH$_3$), 16.14 (C-6), FAB-MS m/z 622.16(M+Na)$^+$, 3.47%; 638.17 (M+K)$^+$, 100%; (C$_{30}$H$_{33}$NO$_{12}$ requires M, 599.20).

III. TLC was performed on Merck Silica Gel 60 F$_{254}$ with detection by charring with sulfuric acid N,N-Dimethylformamide (DMF) was freshly distilled by fractional distillation at reduced pressure and kept over 3 molecular sieves. Light petroleum was the 60°–80° C. fraction. All organic solvents were of p.a. quality from Labscan (Ireland). Concentrations were performed under reduced pressure at temperatures <30° C. (bath). p-((α-Fluoren-9-ylmethoxycarbonyl amino)-2,4-dimethoxybenzyl)phenoxyacetic acid (Rink-linker) and suitably protected N$^\alpha$-Fmoc amino acids were purchased from NovaBiochem (Switzerland), O-(1 H-benzotriazol-1-yl)-N,N,N',N'-tetramethyluronium tetrafluoroborate(TBTU) and 3,4-dihydro-3-hydroxy-4-oxo-1,2,3-benzotriazine (Dhbt-OH) from FLUKA (Switzerland), N-ethylmorpholine from MERCK (Germany). The peptides and the glycopeptides were hydrolysed with 6 mol dm$^{-3}$ HCl at 110° C. for 24 h and the amino acid composition was determined on a Pharmacia LKB Alpha Plus amino acid analyzer. Asn was determined as Asp. NMR spectra were recorded on a Bruker AM-500 or a Bruker AMX-600 MHz spectrometer. The $^1$H and $^{13}$C resonances were assigned by $^1$H, $^{13}$C, $^1$H-$^1$H COSY, $^1$H-1H Double Quantum Filtered Phase Sensitive COSY, $^{13}$C-$^1$H correlation. NMR spectra were recorded in H$_2$O/CD$_3$COOD-mixtures at pH (pD)=2.8 measured at room temperature using a PHM63 Digital pH Meter (Radiometer) equipped with an INGOLD electrode with no correction for isotope effects. HPLC was performed on a Waters system with a 600 controller, a 410 differential refractometer or a 991 photodiode array detector, both equipped with preparative flow cells, and a model 600 pump with modified 80 cm$_3$/min pump heads. The system was fitted with switchable analytical RCM (8×10) and Deltapak (19×300) columns and a preparative radial pack module for columns (50×300 mm) packed with reversed phase C$_{18}$. Solvent system A: 0.1% trifluoroacetic acid (TFA) and B: 0.1% TFA in 90% acetonitrile-10% water, was employed for both analytical (1 cm$^3$/min) and preparative (10 or 20 cm$^3$/min) separations and detection was at 215 nm.

IV. Solid-phase synthesis of Ac-Ser(α-L-Fuc)-Ala-Asp-NH$_2$ and Ac-Ser(β-L-Fuc)-Ala-Asp-NH$_2$ The plastic syringe technique, which is a simple and cheap alternative to automatic peptide synthesizers. A 10 cm$^3$ disposable plastic syringe A (without piston) was fitted with a sintered teflon filter (pore size 70 μm) and the outlet connected to the outlet of a 50 cm$^3$ plastic syringe B via a teflon tube with luer adapters. Syringe B was used as a waste syringe to remove solvents and unused reagents. PEGA-resin (0.386 g, 0.14 mmol/g) was placed in syringe A and allowed to swell in DMF (10 cm$^3$) which was carefully added from the top and removed from the bottom by suction with syringe B. After thorough rinse with DMF (3×5 cm$^3$) Rink-linker (114 mg, 0.21 mmol), TBTU (62 mg, 0.199 mmol) and N-ethyl-morpholine (48 mm$^3$, 0.386 mmol) was dissolved in DMF (2.5 cm$^3$) and after 15 min added to the resin. After 2 h the resin was rinsed with DMF (10×4 cm$^3$), deprotected with 50% morpholine/DMF (3 cm$^3$, 3 min, removed, 3 cm$^3$ 25 min) and washed again(10×3 cm$^3$). N$^\alpha$Fmoc-L-Asp(But)-OPfp (173 mg, 0.3 mmol) and Dhbt-OH (8.8 mg, 0.054 mmol) were dissolved in DMF (4 cm$^3$) and the mixture added to the resin. The acylation time was determined by observation of the yellow color formed between Dhbt-OH and unreacted amino groups. After coupling, the resin was rinsed with DMF (10×3 cm$^3$) before N-Fmoc deprotection and washing as described above. Then N$^\alpha$Fmoc-L-Ala-OPfp (140 mg, 0.3 mmol) and Dhbt-OH (8.8 mg, 0.054 mmol) was added and after 2 h the resin was rinsed, deprotected and rinsed as above. Fmoc-Ser(O-Ac$_3$-a-L-Fuc)-OH (93.2 mg, 0.14 mmol), TBTU (43 mg, 0.13 mmol) and N-ethylmorpholine (36 mm$^3$, 0.26 mmol) was dissolved in DMF (2.5 cm$^3$) and after 15 min added to the resin. After 20 h the resin was rinsed with DMF, deprotected and rinsed as described above. After acetylation with 10% acetic anhydride in DMF for 30 min peptide-resin was rinsed with DMF (15×3 cm3) and dichloromethane (5×3 cm$^3$) and lyophilized before cleavage of the peptide from the solid support with TFA/water to yield crude glycopeptide. The cleavage from the resin was performed with TFA/water (10/1, 22 cm$^3$, 1.3 h, ambient temperature (essentially 1 major peak (80%) and 1 minor peak (20%) in HPLC, longer reaction time gave more by-products)) and after filtration, washing with 90% TFA, evaporation and several triturations with diethylether, the precipitated crude glycopeptide, tri-O-acetate (60 mg) was purified by preparative HPLC using 10 cm$^3$ min$^{-1}$ 0% solvent B for 20 min, followed by a linear gradient of 10–50% solvent B during 100 min (retention time 90 min). The yield of Ac-Ser(Ac$_3$-a-L-Fuc)-Ala-Asp-NH$_2$ after HPLC was 20.7 mg (64%) ($^1$H NMR data are presented in table 1) and 4 mg (12%) of the compound lacking N$^\alpha$-acetylation according to NMR. The β-linked compound, Ac-Ser(O-Ac$_3$-β-L-Fuc)-Ala-Asp-NH$_2$ was prepared in a similar way on 398 mg of resin with a yield of 28.4 mg (85%) ($^1$H NMR data are presented in table 1) after preparative HPLC (eluting as a single peak in the analytical HPLC of the crude product). The purified acetylated glycopeptide, Ac-Ser(Ac$_3$-a-L-Fuc)-Ala-Asp-NH$_2$ was dissolved in dry methanol (1 mg cm$^{-3}$) and sodium methoxide in methanol (1 mol dm$^{-3}$) was added until a wetted pH-paper indicated pH 11. The mixture was stirred at ambient temperature for 45 h following the reaction by HPLC, then neutralized with small pieces of solid CO$_2$ and concentrated. The residue was dissolved in water (1 mg cm$^{-3}$) and purified by preparative HPLC using 10 cm$^3$ min$^{-1}$ 0% solvent B for 15 min, followed by a linear gradient of 0–20% solvent B during 50 min and then 100% solvent B (retention time 20 min). The yield of Ac-Ser(α-L-Fuc)-Ala-Asp-NH$_2$ after HPLC was 14.1 mg (87%, single peak). Deacetylation of Ac-Ser(Ac$_3$-β-L-Fuc)-Ala-Asp-NH$_2$ with sodium methoxide as described above, followed by purification by preparative HPLC using the same gradient yielded 21.8 mg (97%, single peak at 30 min). $^1$H NMR data are presented in Table 1.

binding of selectins to 2,3-sLex glycolipid. An ELISA assay consisting of evaporating 2.3 sLex glycolipid, at 25 picomoles per well, onto microtiter wells, and then washing the excess off with water was used. The wells were blocked with 5% BSA at room temperature for an hour and then washed with PBS containing 1 mM calcium ion. While the plate was

TABLE 1

$^1$H-NMR chemical shifts (ppm) and coupling constants (Hz) of glyco-tripeptides, measured at 500 MHz or 600 MHz at 300 K.
Reference: TMS (in d$_6$DMSO) or internal acetic acid at 2.03 ppm.

|  |  | Ac-Ser(Ac$_3$-a-L-Fuc)-Ala—Asp—NH$_2$[a] | Ac-Ser(Ac$_3$-β-L-Fuc)-Ala—Asp—NH$_2$[a] | Ac-Ser(α-L-Fuc)-Ala—Asp—NH$_2$[b] | Ac-Ser(β-L-Fuc)-Ala—Asp—NH$_2$[b] |
|---|---|---|---|---|---|
| Asp$^3$ | NH1 | 7.08 | 7.05 | 7.053 | 7.066 |
|  | NH1' | 7.12 | 7.12 | 7.372 | 7.327 |
|  | N$^\alpha$H | 8.03 (6) | 7.96 (6) | 8.105 (8.1) | 8.070 (8.0) |
|  | α | 4.14 | 4.01 | 4.723 | 4.743 |
|  | β | 2.52 (7;15) | 3.911 (7;15) | 2.855 (7.8;16.8) | 2.869 (7.6;17.0) |
|  | β' | 2.67 (5) | 2.67 (5) | 2.948 (5.4) | 2.951 (5.4) |
| Ala$^2$ | N$^\alpha$H | 8.15 (6) | 8.21 (6) | 8.215 (6.3) | 8.270 (6.0) |
|  | α | 4.20 | 4.16 | 4.418 | 4.377 |
|  | β | 1.23 (7) | 1.21 (7) | 1.380 (7.5) | 1.394 (7.2) |
| Ser$^1$ | N$^\alpha$H | 8.15 (5) | 8.21 (6) | 8.530 (7.2) | 8.288 (6.6) |
|  | α | 4.50 | 4.45 | 4.580 | 4.538 |
|  | β | 3.68 (8) | 3.58 (8;10) | 3.670 (3.8;10.0) | 4.040 (4.4;16) |
|  | β' | 3.68 (4) | 3.93 (4) | 4.076 (3.6) | 4.070 (3.0) |
| Fuc | H-1 | 5.10 (4) | 4.62 (8) | 4.885 (2.6) | 4.377 (7.8) |
|  | H-2 | 4.92 (9.8) | 4.87 (9.6) | 3.858 (—) | 3.547 (9.6) |
|  | H-3 | 5.15 (—) | 5.04 (4) | 3.810 (—) | 3.662 (3.2) |
|  | H-4 | 5.15 (—) | 5.10 (—) | 3.798 | 3.762 |
|  | H-5 | 4.42 (6.5) | 4.43 (6.5) | 3.880 (6.9) | 3.762 (6.9) |
|  | H-6 | 1.05 | 1.08 | 1.208 | 1.282 |
|  | O-Ac | 1.88 | 1.86 |  |  |
|  | O-Ac | 1.92 | 1.91 |  |  |
|  | O-Ac | 2.12 | 2.12 |  |  |
|  | N-Ac | 2.03 | 1.99 | 2.083 | 2.070 |

[a]2 mg in d$_6$DMSO (600 mm$^3$)
[b]2 mg in 10% DC$_3$COOD/H$_2$O (600 mm$^3$, pH 2.5)

V. Synthesis and Analysis of Additional Peptides

The methods of Examples 1-IV were utilized to synthesize and analyze the following compounds:
Ac-Ser(α-L-Fuc)-Phe-Asp-NH$_2$
Ac-Ser(α-L-Fuc)-Ser-Asp-NH$_2$
Ac-Ser(α-L-Fuc)-Asn-Asp-NH$_2$
Ac-Ser(α-L-Fuc)-Asp-Asp-NH$_2$
Ac-Ser(α-L-Fuc)-Leu-Asp-NH$_2$
Ac-Ser(α-L-Fuc)-Gly-Asp-NH$_2$
Ac-Ser(α-L-Fuc)-Pro-Asp-NH$_2$
Ac-Ser-Arg-Asp-NH$_2$
Ac-Ser-Phe-Asp-NH$_2$
Ac-Ser-Asn-Asp-NH$_2$
Ac-Ser-Ser-Asp-NH$_2$
Ac-Ser(β-L-Fuc)-Arg-Asp-N H$_2$
Ac-Ser(α-L-Fuc)-Arg-Asp-NH$_2$
Ac-Ser(β-L-Fuc)-Phe-Asp-NH$_2$
Ac-Ser(β-L-Fuc)-Ser-Asp-NH$_2$
Ac-Ser(β-L-Fuc)-Asn-Asp-NH$_2$
Ac-Ser(β-L-Fuc)-Asp-Asp-NH$_2$
Ac-Ser(β-L-Fuc)-Leu-Asp-NH$_2$
Ac-Ser(β-L-Fuc)-Gly-Asp-NH$_2$
Ac-Ser(β-L-Fuc)-Pro-Asp-NH$_2$ NMR spectra for the above compounds are presented in FIGS. 9A–B, 10A–B, 11A–B and 12–31.

VI. Inhibition assays

Competitive inhibition assays were performed to determine the ability of various glycopeptides to inhibit the binding of selectins to 2,3-sLex glycolipid. An ELISA assay consisting of evaporating 2.3 sLex glycolipid, at 25 picomoles per well, onto microtiter wells, and then washing the excess off with water was used. The wells were blocked with 5% BSA at room temperature for an hour and then washed with PBS containing 1 mM calcium ion. While the plate was blocked, biotin labelled goat F(ab')$_2$ IgG (Fc specific) and streptavidin-alkaline phosphatase diluted 1:1500 in 1% BSA-PBS (1 mM calcium ion) were combined with the L-Selectin-lgG chimera (L91-10) at 200 ng/mL and incubated at 37° C. for 15 minutes to allow a complex to form. This provides a soluble "multivalent" receptor. The potential inhibitors are added to the soluble receptor and allowed to react at 37° C. for 45 minutes. It is assumed that the optimal binding of soluble phase receptor/ligand occurs within this time frame. The solutions are then placed in the microtiter wells that have been washed after being blocked. The plates are then incubated at 37° C. for 45 minutes to allow the soluble receptor to bind to the known natural ligand. The positive control is the signal produced by soluble "multivalent" receptor reacted with only the ligand evaporated to the microtiter well. This is considered "100% binding." The signal produced by receptor previously reacted with inhibitor is divided by the signal produced by the positive control, multiplied by 100, to calculate % receptor bound in the presence of the inhibitor. The reciprocal of this is % inhibition.

Figure 4:
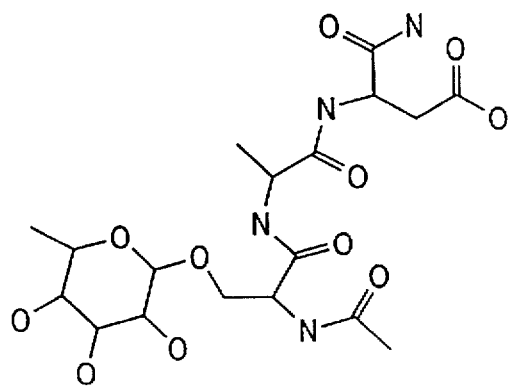
FIG. 4 shows a diagram of glycotripeptides Ac-Ser(L-Fuc)-Ala-Asp-NH$_2$. The fucose can be in the α or β configuration.

Results of the competitive inhibition assays are shown in FIGS. 5–8. The results demonstrate that the various glycopeptides synthesized inhibit the binding of the L, P and E-selectins differentially and specifically in a concentration dependent manner. FIG. 4 is a diagram of the compounds used in the competitive inhibition assays of FIGS. 5 and 6. The glycopeptide names and corresponding identification letters are found in Table 2 below.

TABLE 2

| Identification Letter | Compound |
| --- | --- |
| A | Ac—Ser(α-L-Fuc)-Ala—Asp—NH$_2$ |
| B | Ac—Ser(β-L-Fuc)-Ala—Asp—NH$_2$ |
| C | Ac—Ser—Phe—Asp—NH$_2$ |
| D | Ac—Ser—Asu—Asp—NH$_2$ |
| E | Ac—Ser(α-L-Fuc)-Gly—Asp—NH$_2$ |
| F | Ac—Ser—Ser—Asp—NH$_2$ |
| G | Ac—Ser(β-L-Fuc)-Arg—Asp—NH$_2$ |
| H | Ac—Ser(α-L-Fuc)-Arg—Asp—NH$_2$ |

Figure 5:
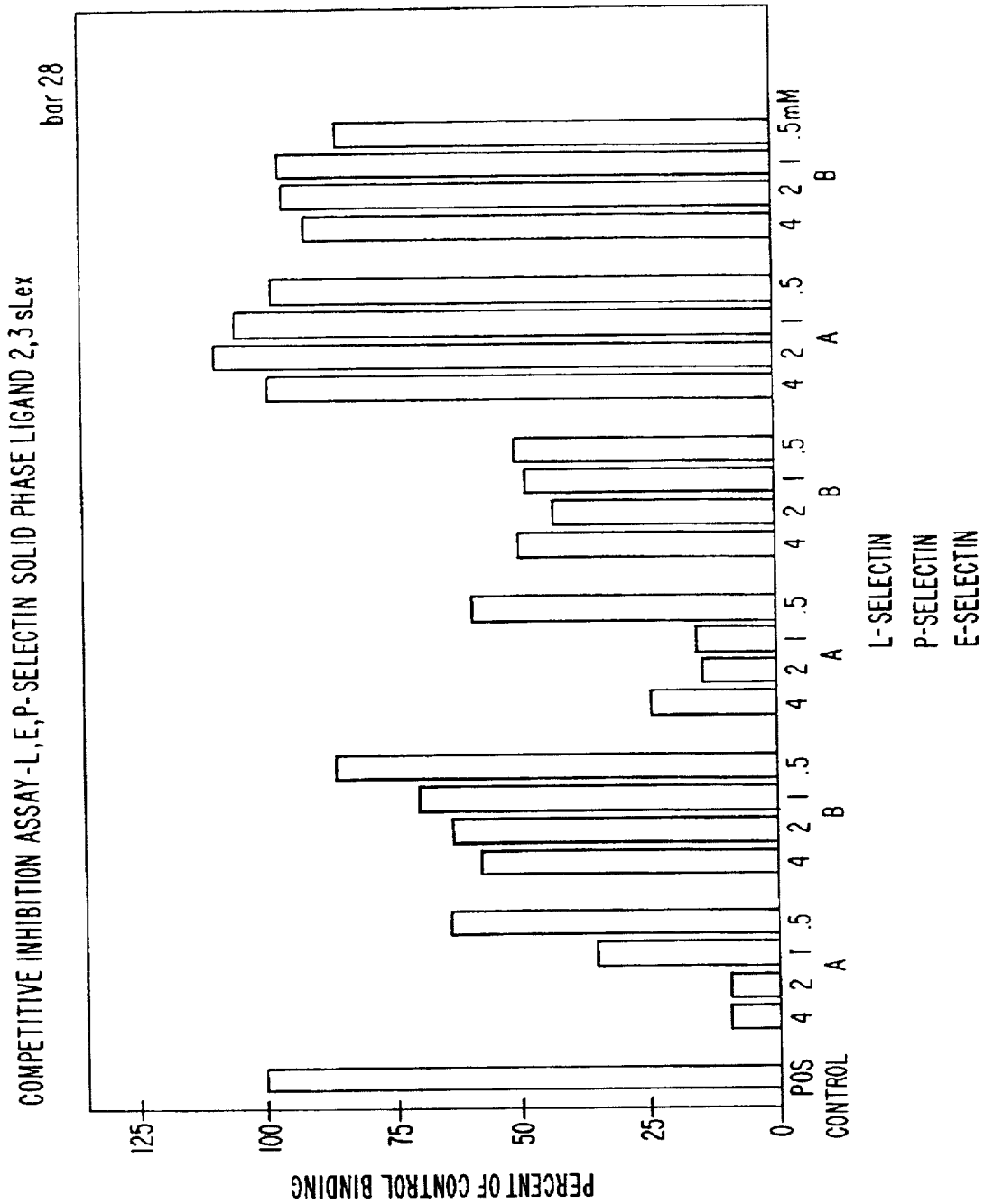
FIG. 5 shows the results from a competitive inhibition assay of L, E and P selectins with Ac-Ser(α-L-Fuc)-Ala-Asp-NH$_2$ (A) and Ac-Ser(β-L-Fuc)-Ala-Asp-NH$_2$ (B).
Figure 6:
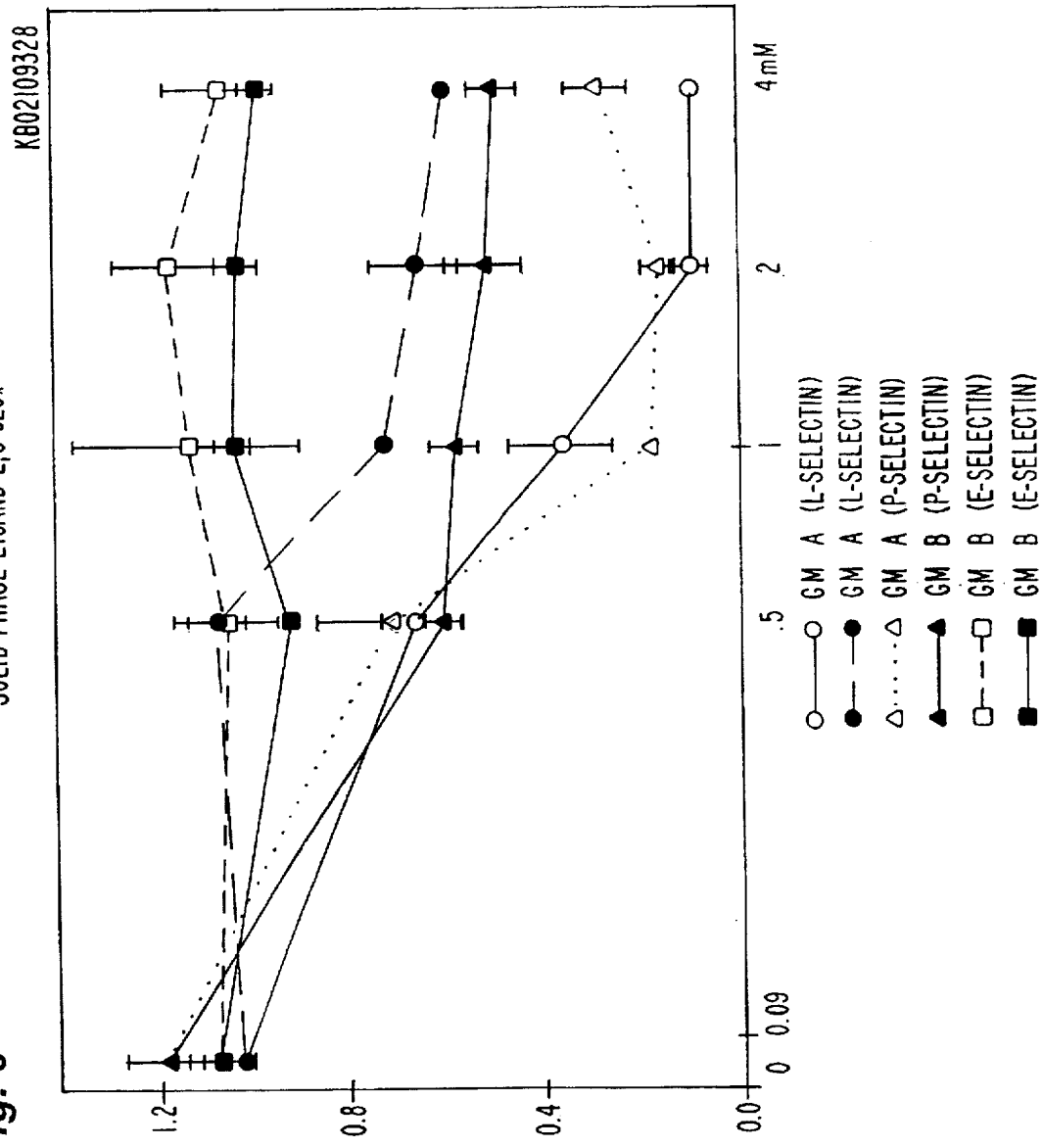
FIG. 6 shows the results from a competitive inhibition assay of L, E and P selectins with Ac-Ser(α-L-Fuc)-Ala-Asp-NH$_2$ (A) and Ac-Ser(β-L-Fuc)-Ala-Asp-NH$_2$ (B).
Figure 7:
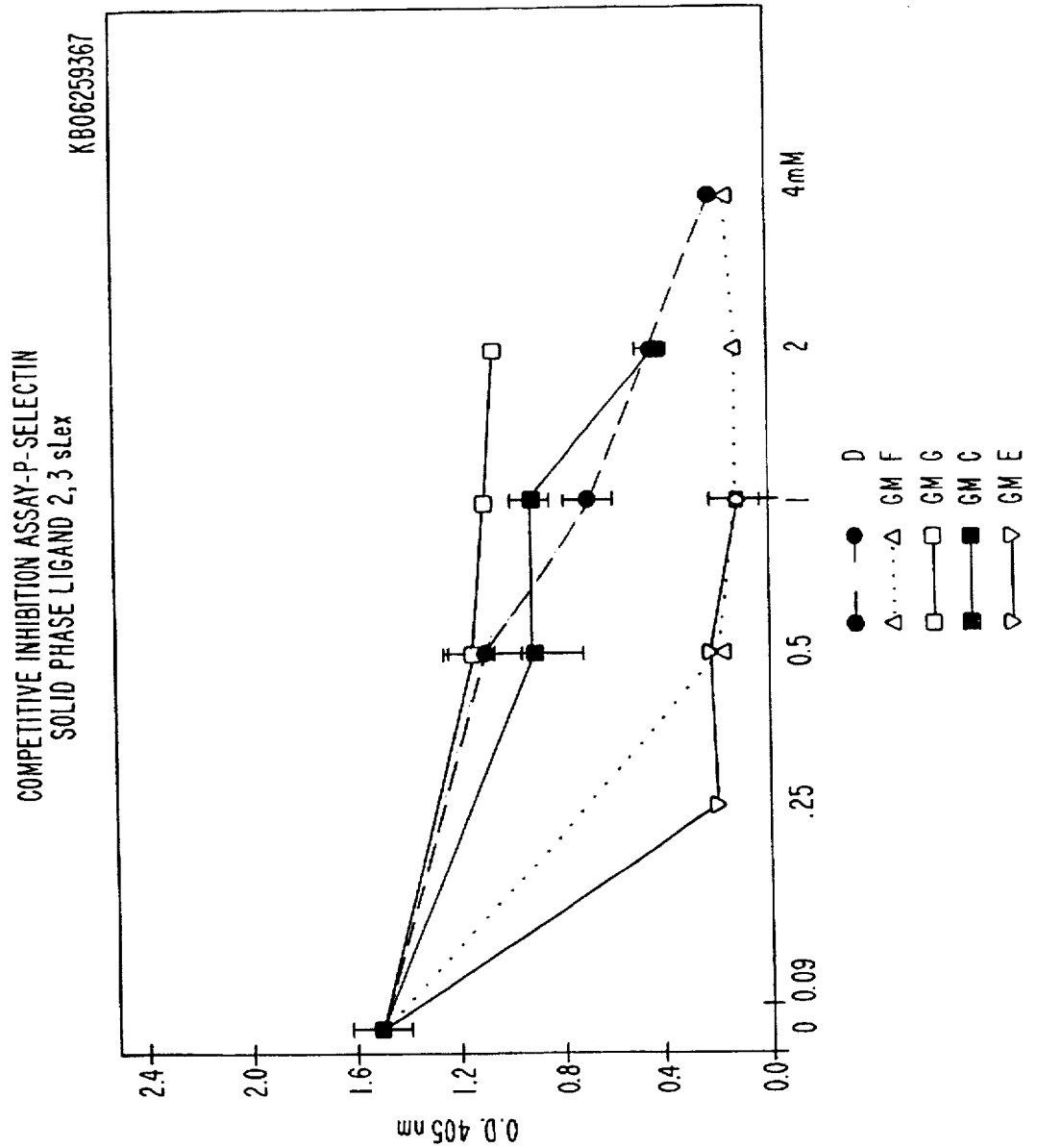
FIG. 7 shows the results from a competitive inhibition assay of P-selectin with: C: Ac-Ser-Phe-Asp-NH$_2$; D: Ac-Ser-Asn-Asp-NH$_2$; E: Ac-Ser(α-L-Fuc)-Gly-Asp-NH$_2$; F: Ac-Ser-Ser-Asp-NH$_2$ and G: Ac-Ser(β-L-Fuc)-Arg-Asp-NH$_2$ together with 2.3 SLex glycolipid.

FIG. 5 demonstrates the differential effects of compounds A and B on the inhibition of binding of L-, P- and E-selection to 2,3 sLex. Both compounds A and B have little effect on the binding of E-selectin to 2,3 sLex glycolipid. Ac-Ser(a-L-Fuc)-Ala-Asp-NH$_2$ inhibits the binding of L-selectin to 2,3 sLex at 2 and 4 mm to a greater extent than does Ac-Ser(β-L-Fuc)-Ala-Asp-NH$_2$ FIG. 7 illustrates the differential effects of different concentrations of compounds C, D, E, F and G on the binding of P selectin to 2,3 sLex glycolipid.

Figure 8:
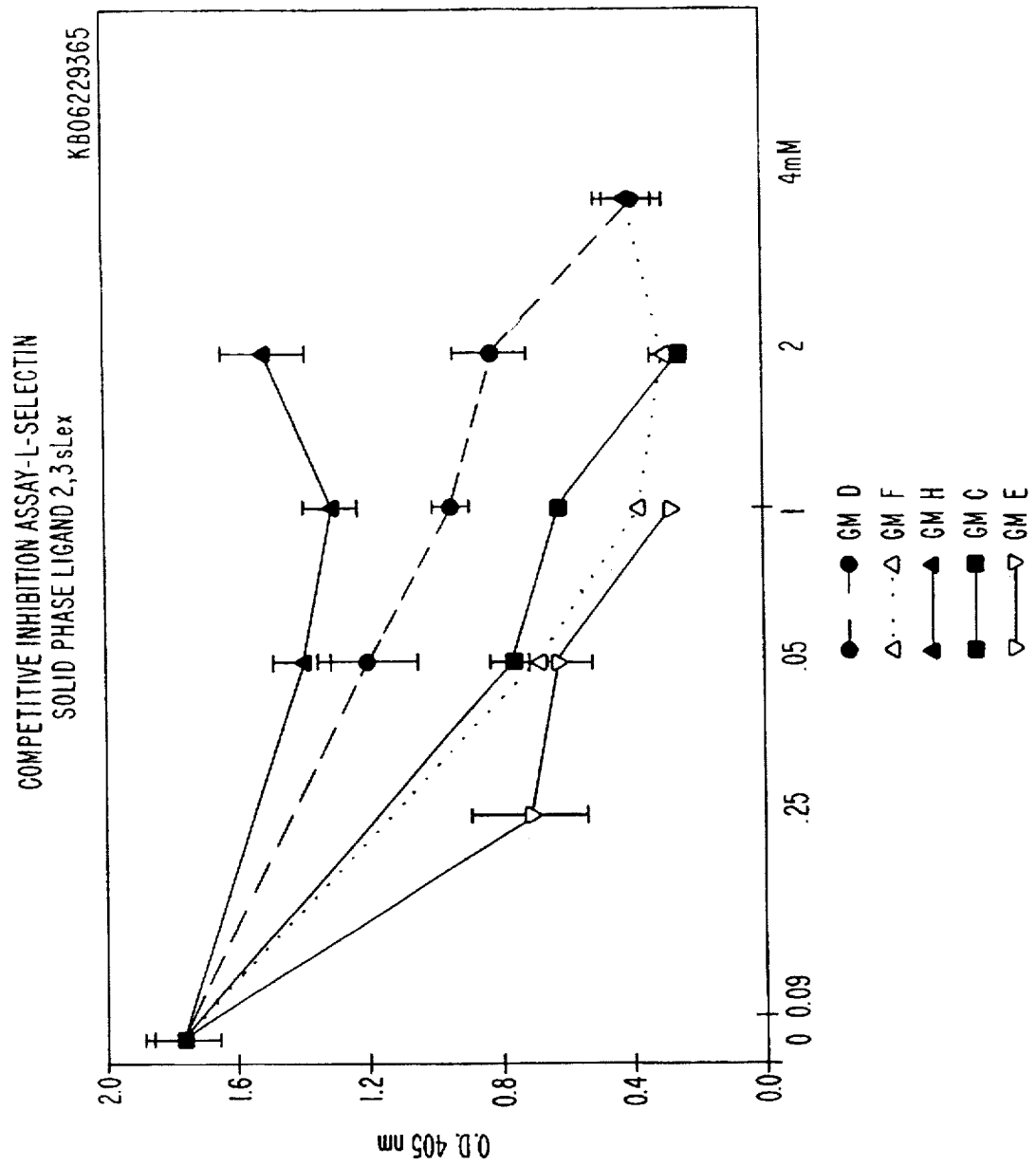
FIG. 8 shows the results from a competitive inhibition assay of L-selectin with: C: Ac-Ser-Phe-Asp-NH$_2$; D: Ac-Ser-Asn-Asp-NH$_2$; E: Ac-Ser(α-L-Fuc)-Gly-Asp-NH$_2$; F: Ac-Ser-Ser-Asp-NH$_2$ and H: Ac-Ser(α-L-Fuc)-Arg-Asp-NH$_2$ together with 2.3 SLex glycolipid.
Figures 9A, 9B:
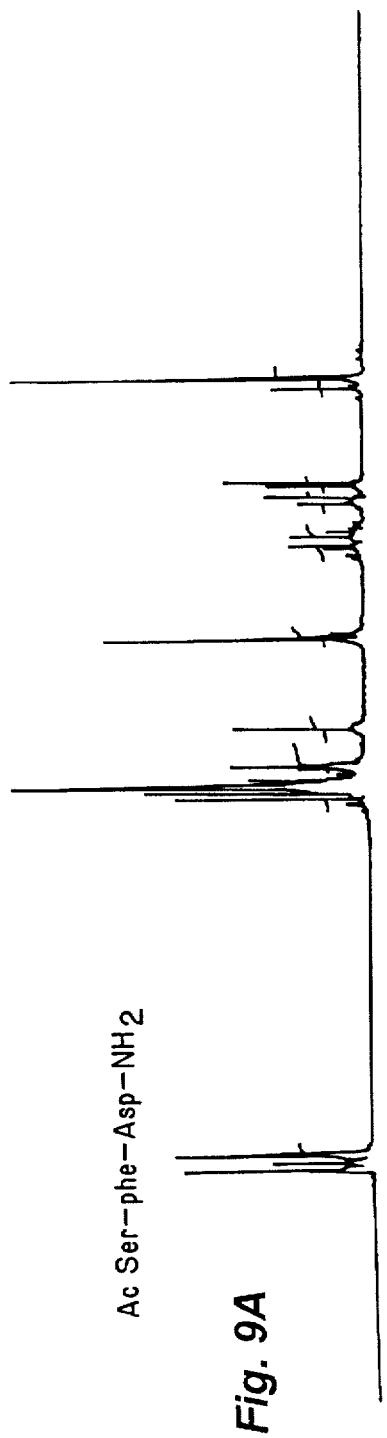
FIG. 9A is an NMR spectrum of Ac-Ser-Phe-Asp-NH$_2$.
FIG. 9B is an NMR spectrum of Ac-Ser-Asn-Asp-NH$_2$.
Figure 11A:
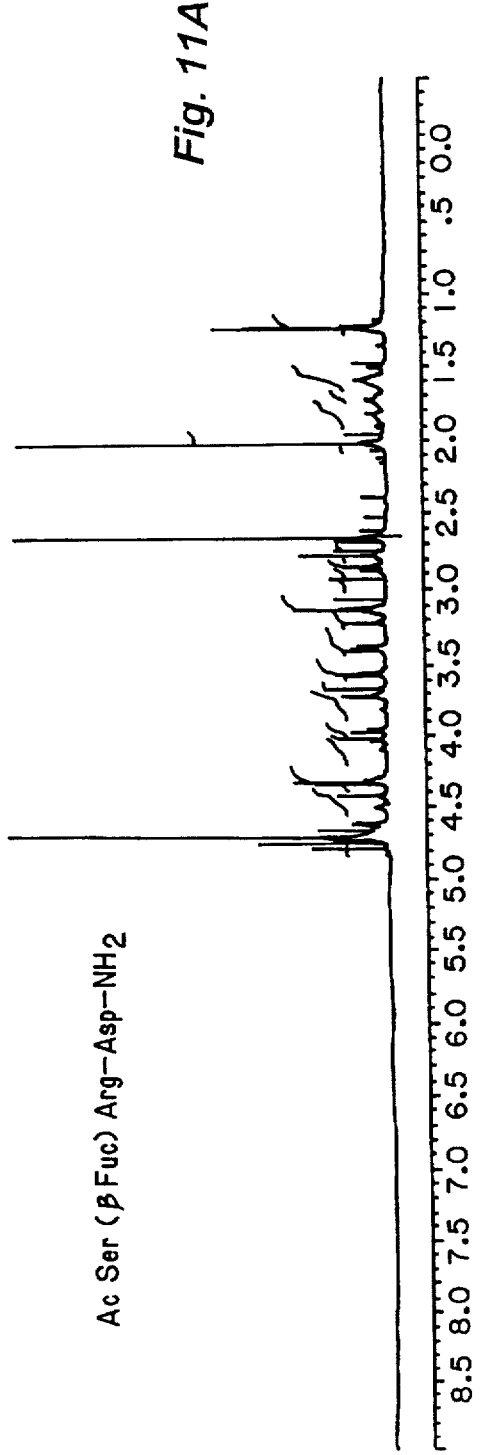
FIG. 11A is an NMR spectrum of Ac-Ser(β-L-Fuc)-Arg-Asp-NH$_2$.
Figure 11B:
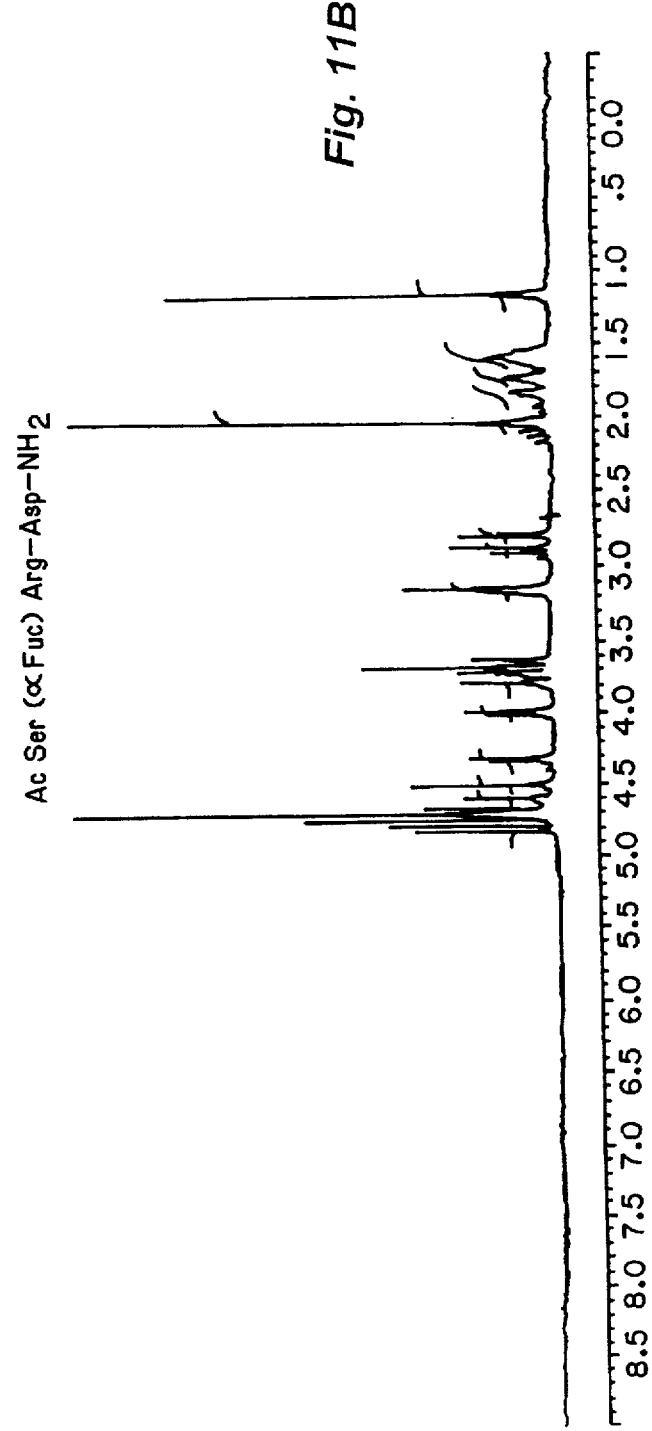
FIG. 11B is an NMR spectrum of Ac-Ser(α-L-Fuc)-Arg-Asp-NH$_2$.
Figure 12:
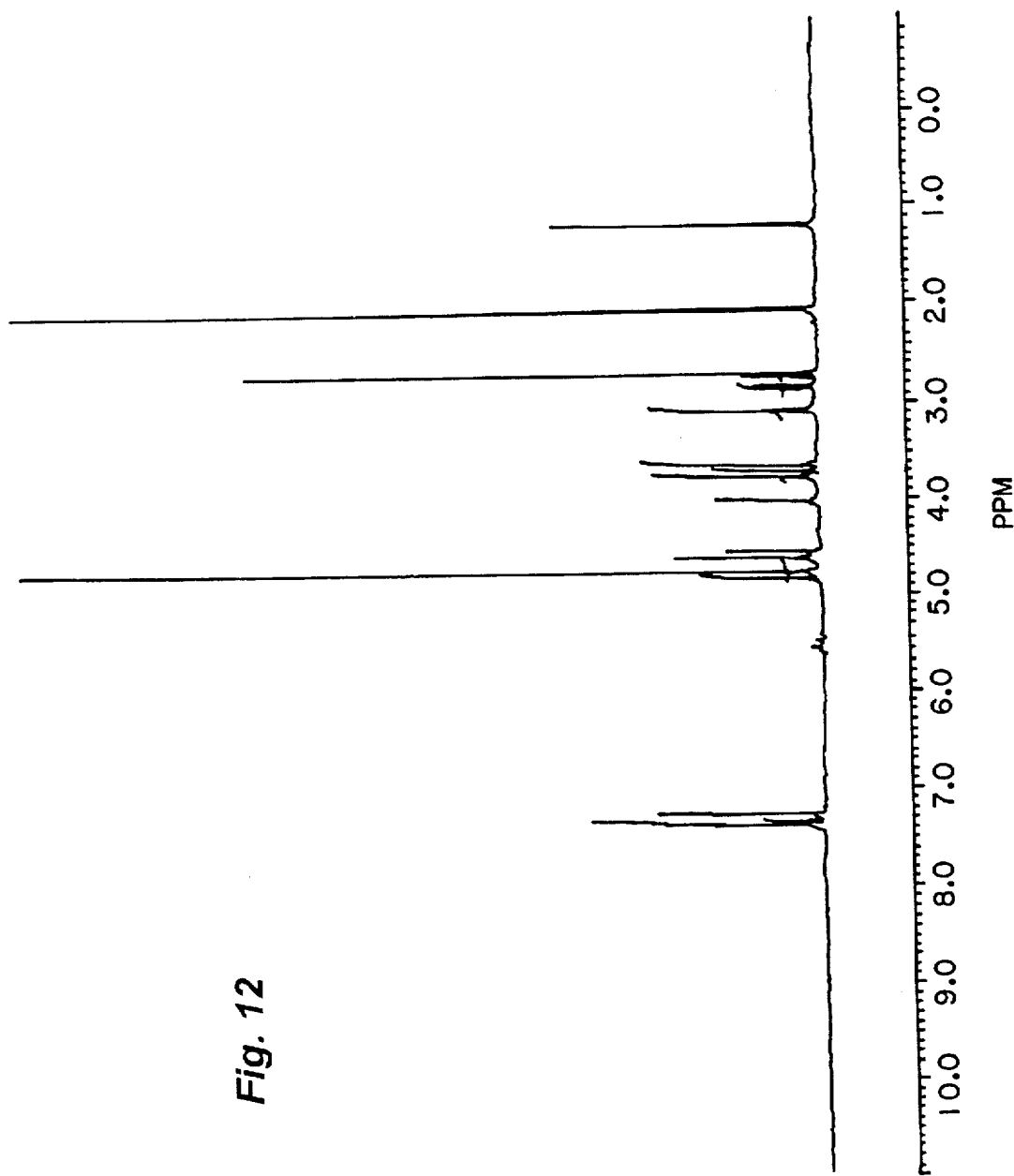
FIG. 12 is an NMR spectrum of Ac-Ser(α-L-Fuc)-Phe-Asp-NH$_2$.
Figure 13:
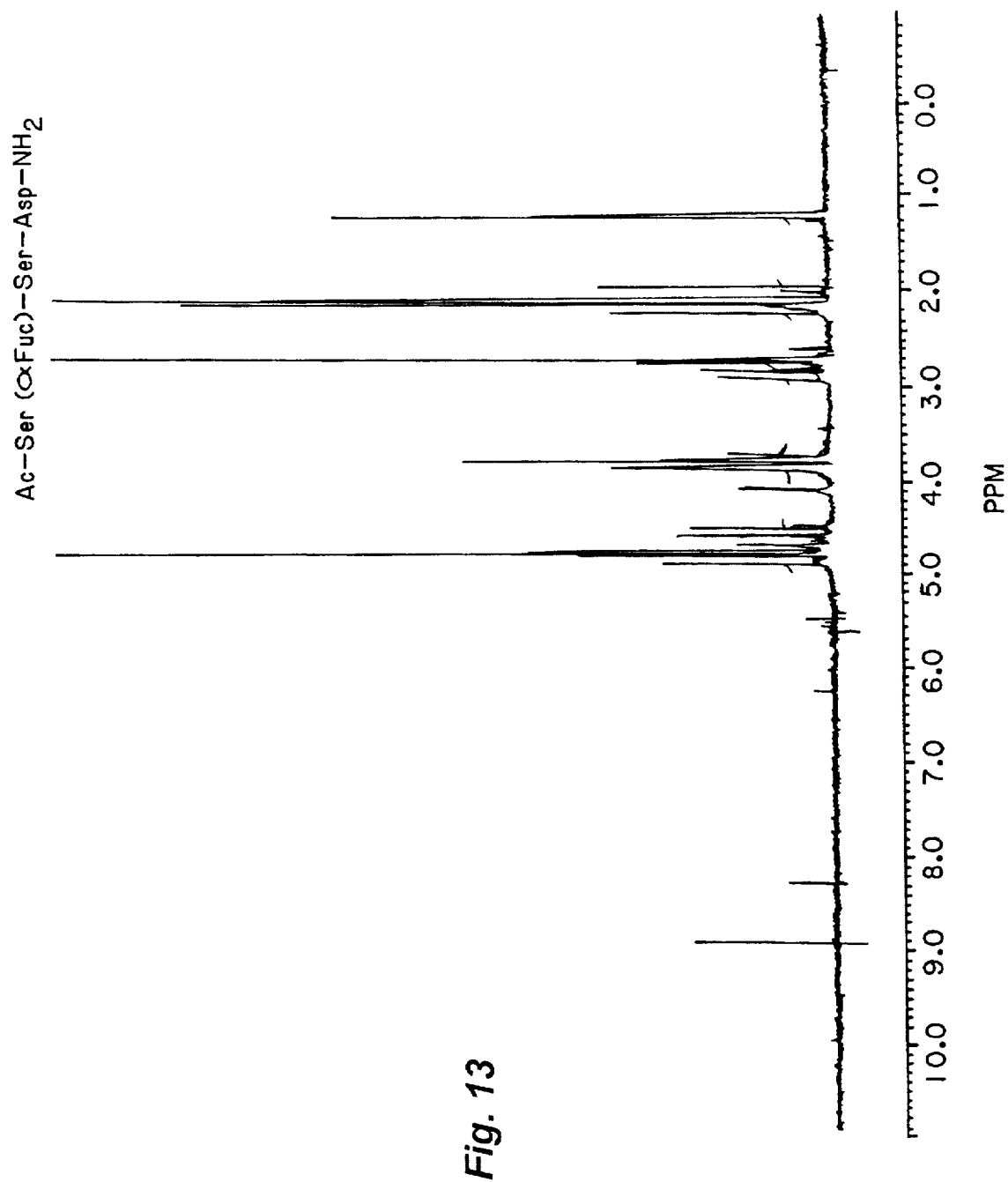
FIG. 13 is an NMR spectrum of Ac-Ser(α-L-Fuc)-Ser-Asp-NH$_2$.
Figure 14:
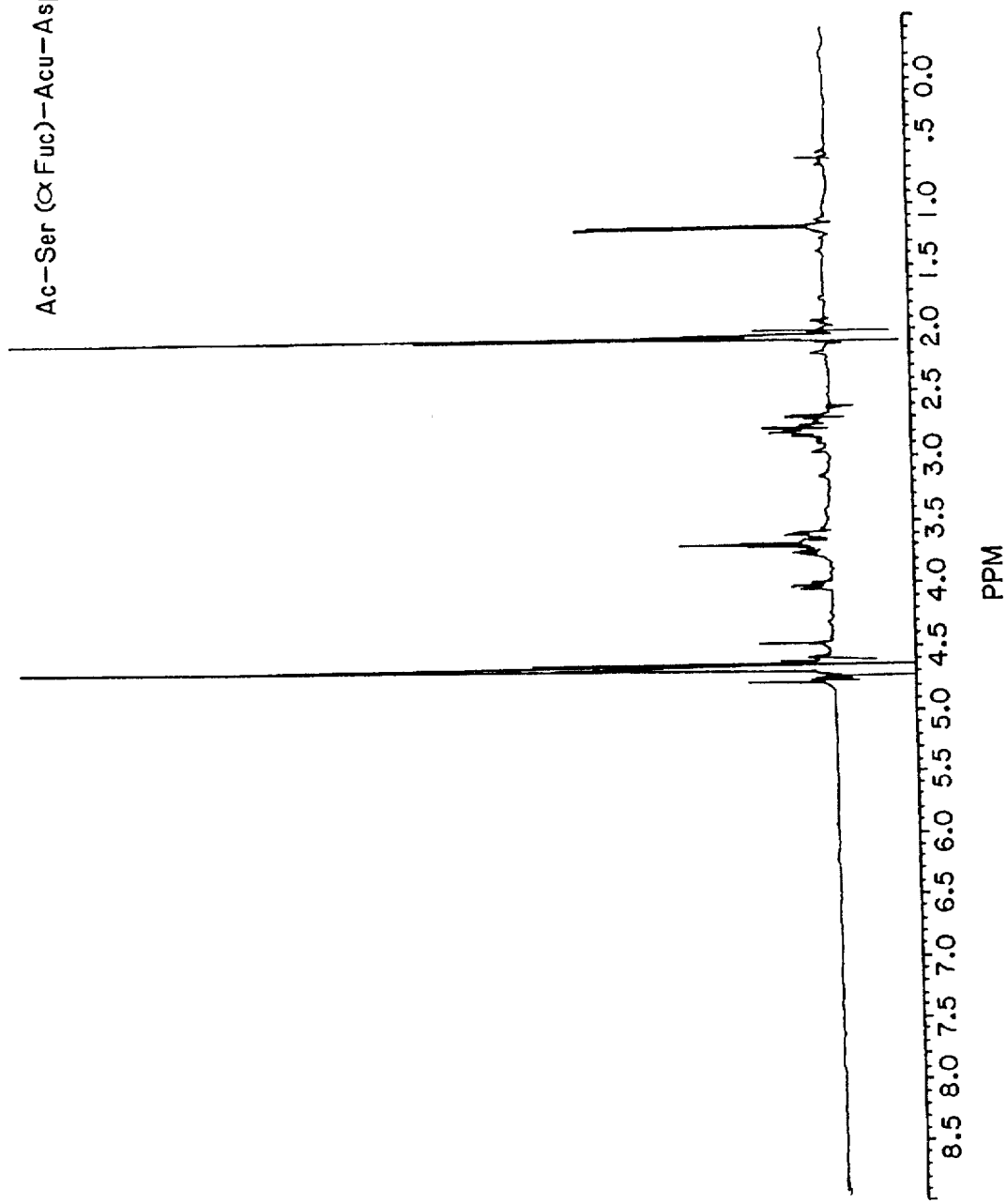
FIG. 14 is an NMR spectrum of Ac-Ser(α-L-Fuc)-Asn-Asp-NH$_2$.
Figure 15:
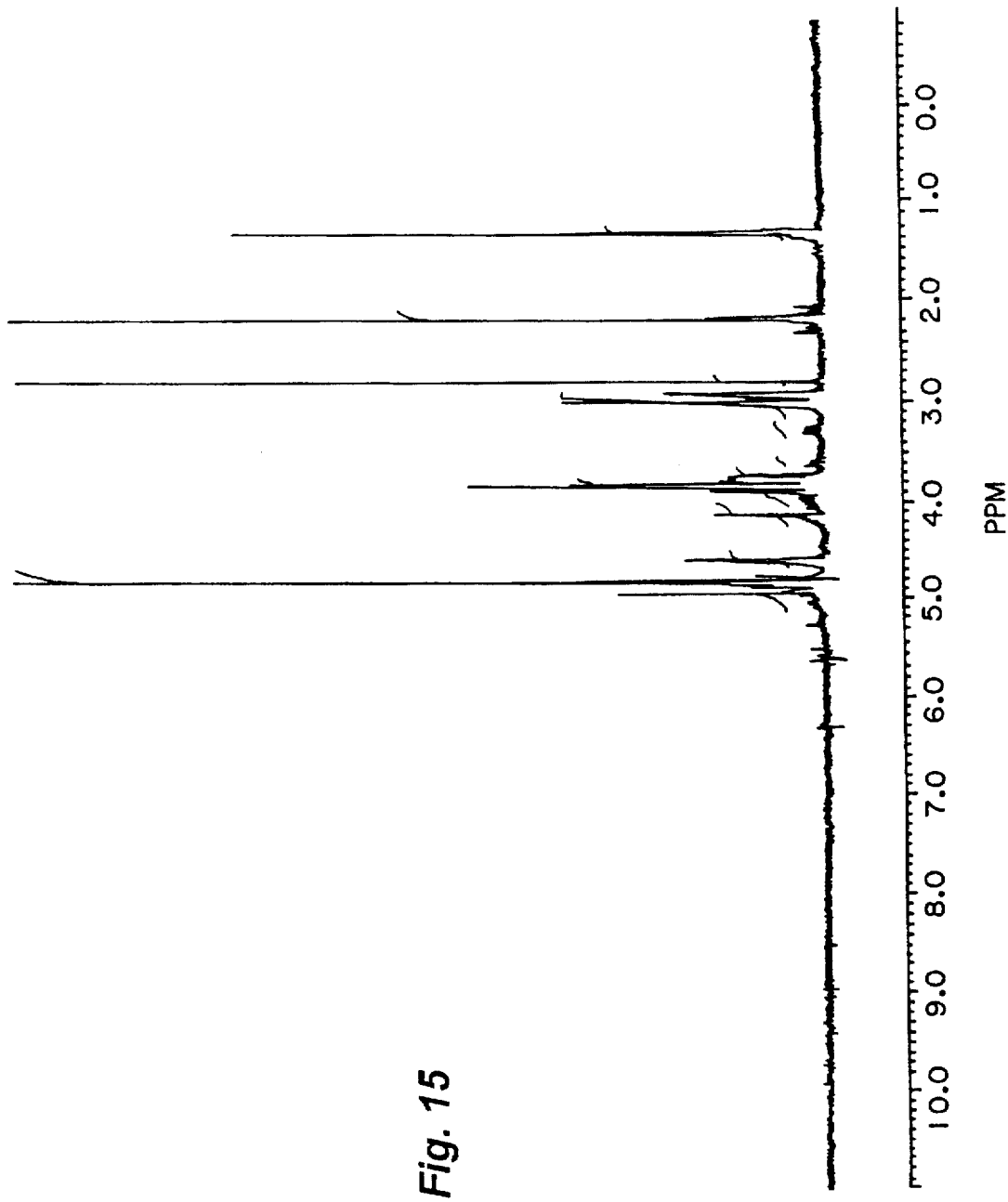
FIG. 15 is an NMR spectrum of Ac-Ser(α-L-Fuc)-Asp-Asp-NH$_2$.
Figure 16:
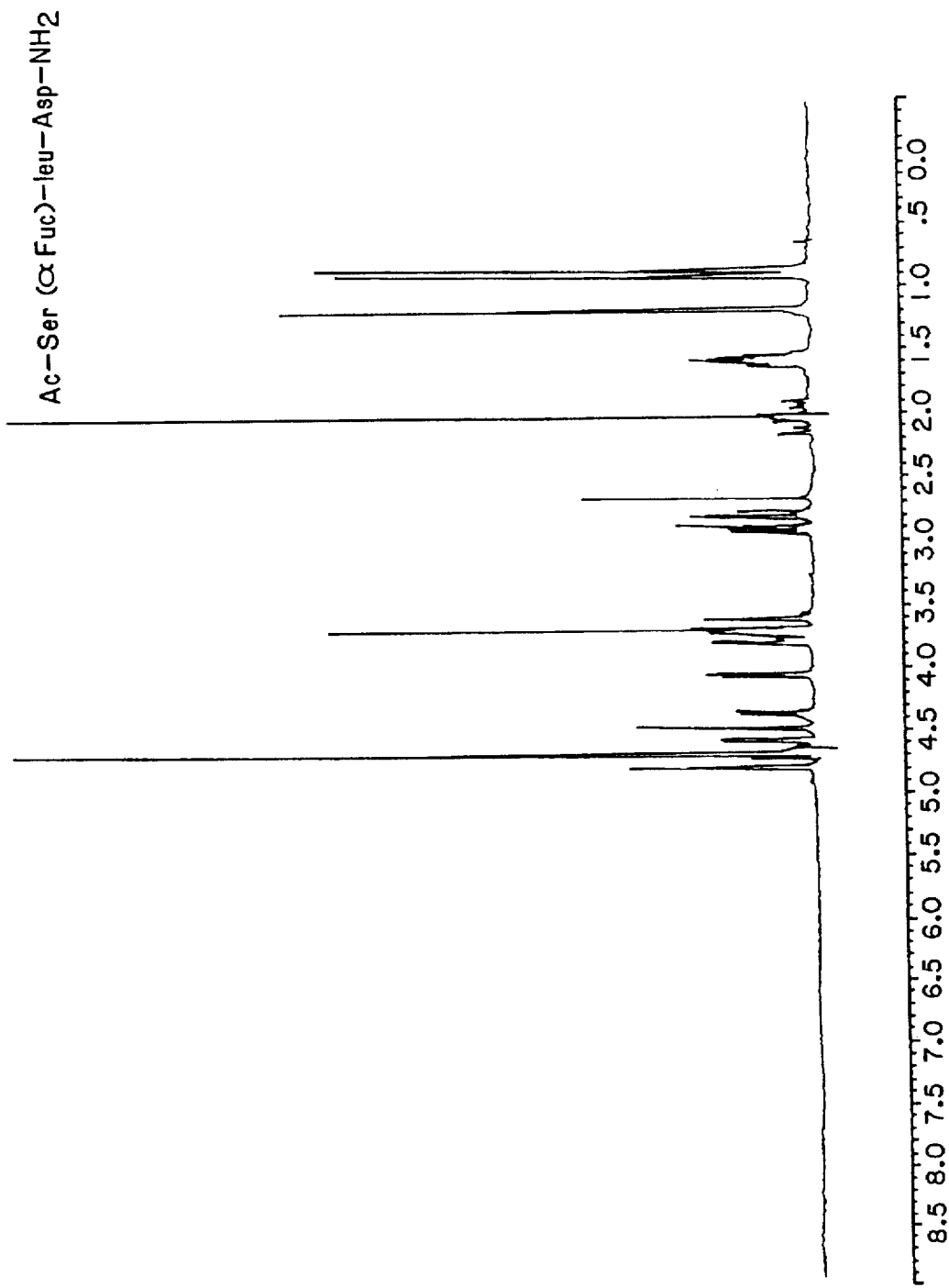
FIG. 16 is an NMR spectrum of Ac-Ser(α-L-Fuc)-Leu-Asp-NH$_2$.
Figure 17:
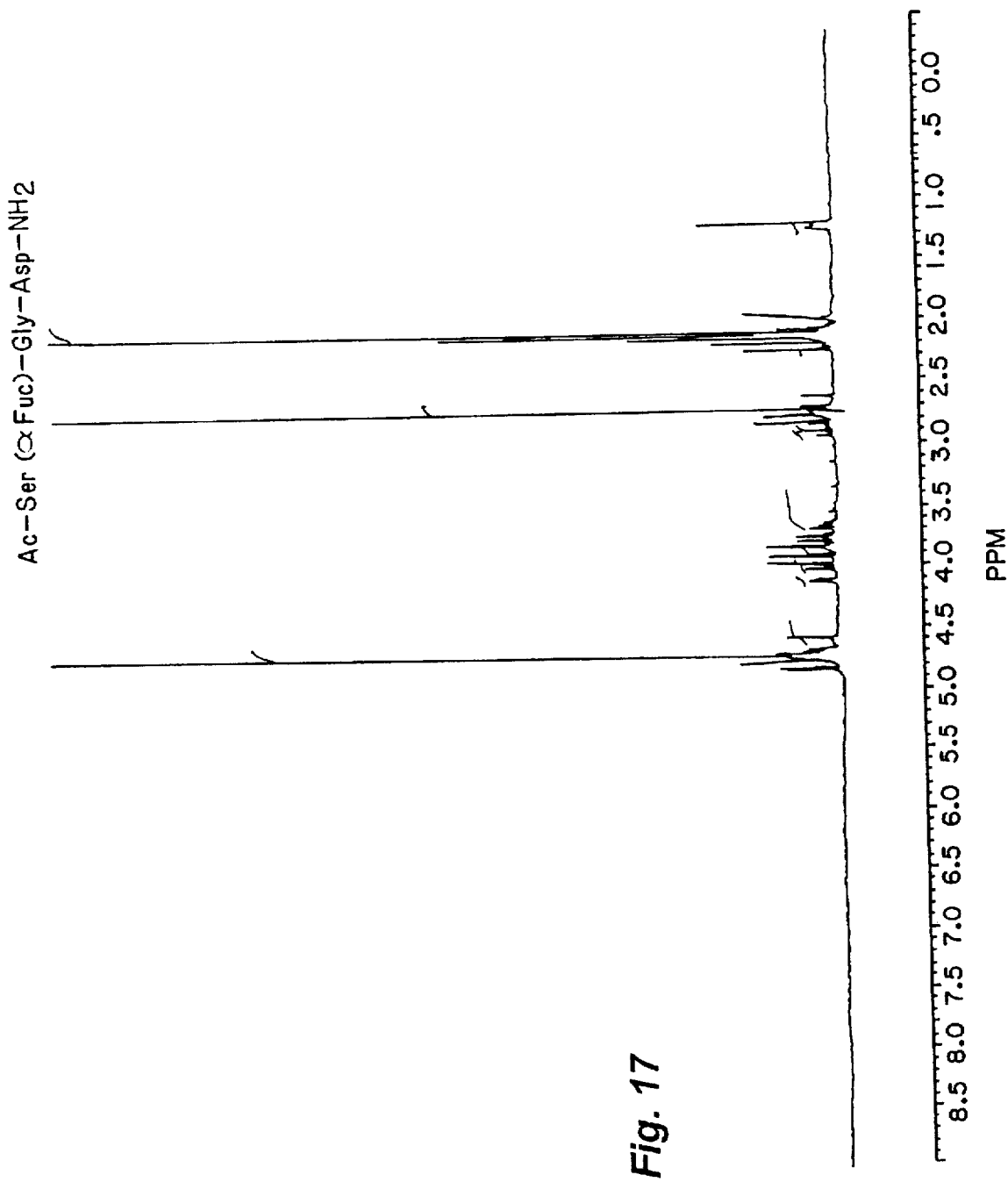
FIG. 17 is an NMR spectrum of Ac-Ser(α-L-Fuc)-Gly-Asp-NH$_2$.
Figure 18:
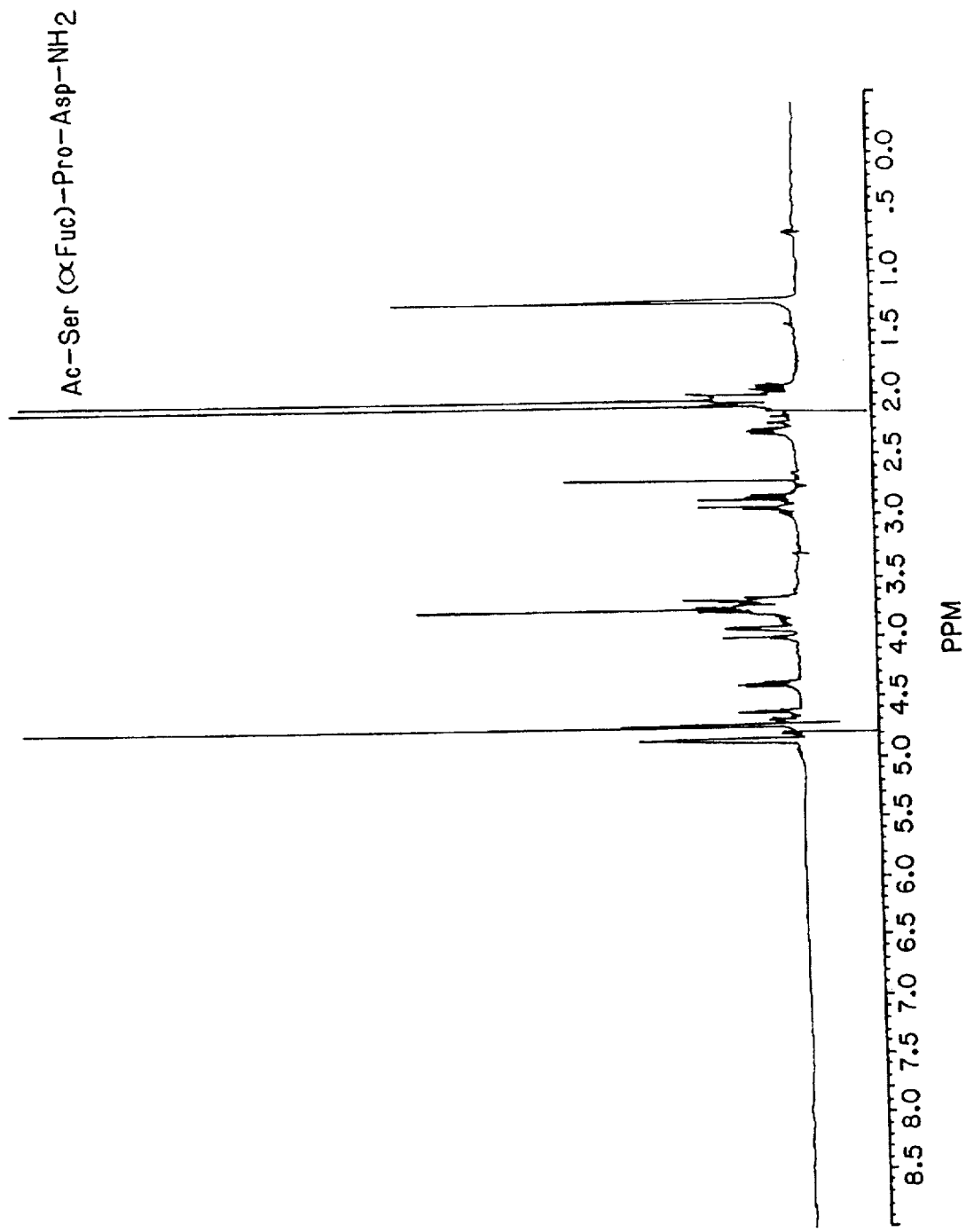
FIG. 18 is an NMR spectrum of Ac-Ser(α-L-Fuc)-Pro-Asp-NH$_2$.
Figure 19:
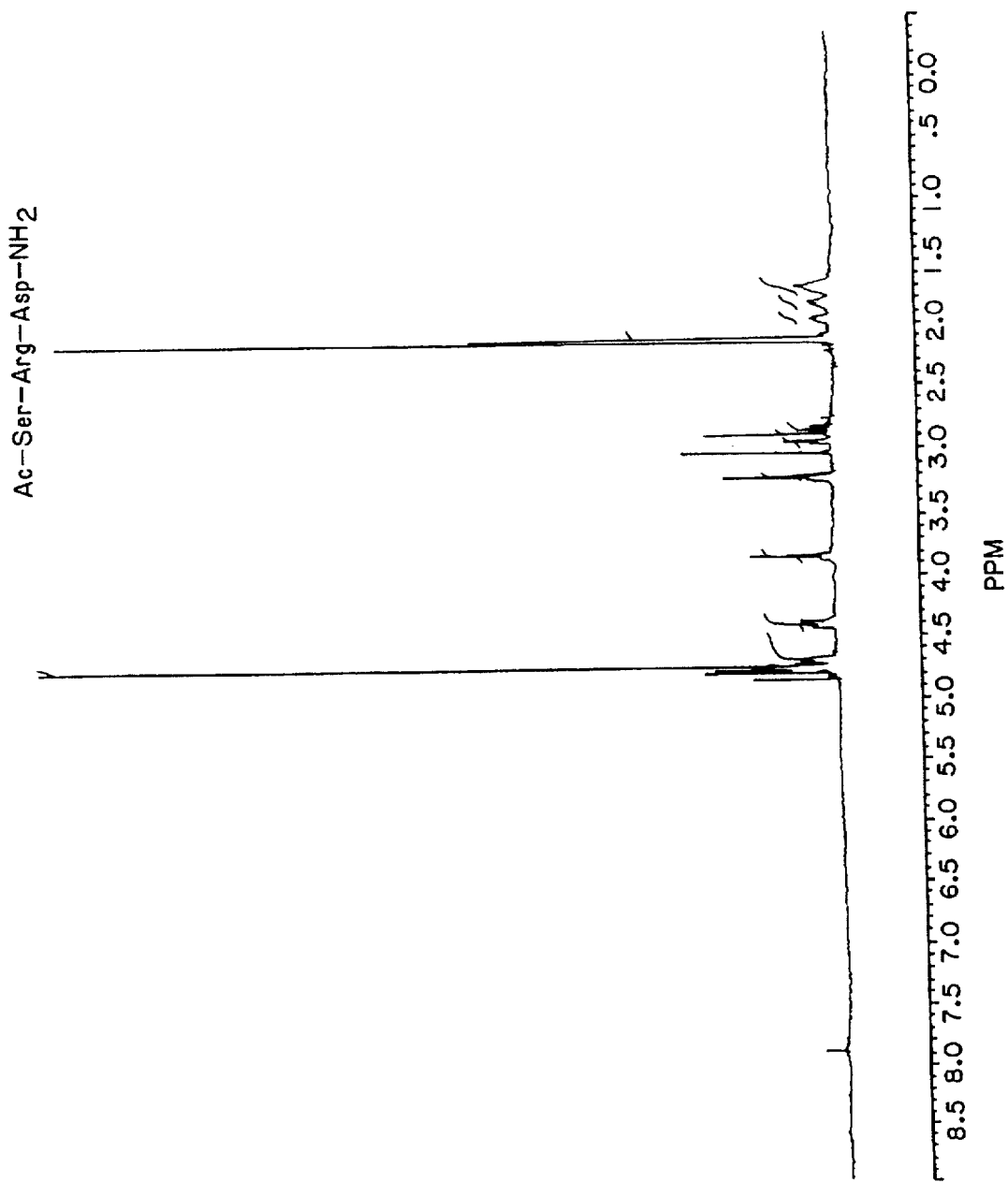
FIG. 19 is an NMR spectrum of Ac-Ser-Arg-Asp-NH$_2$.
Figure 20:
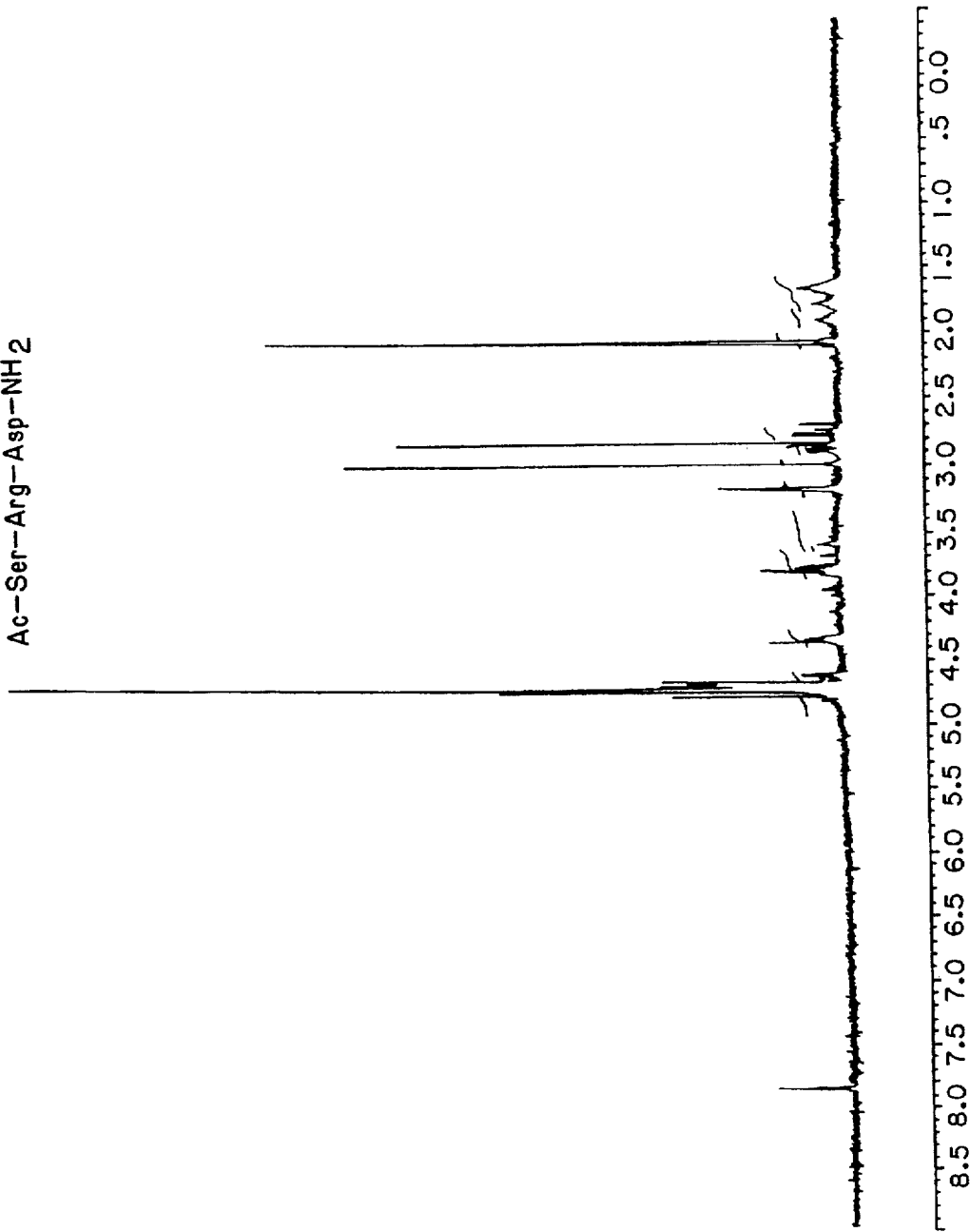
FIG. 20 is an NMR spectrum of Ac-Ser-Arg-Asp-NH$_2$.
Figure 21:
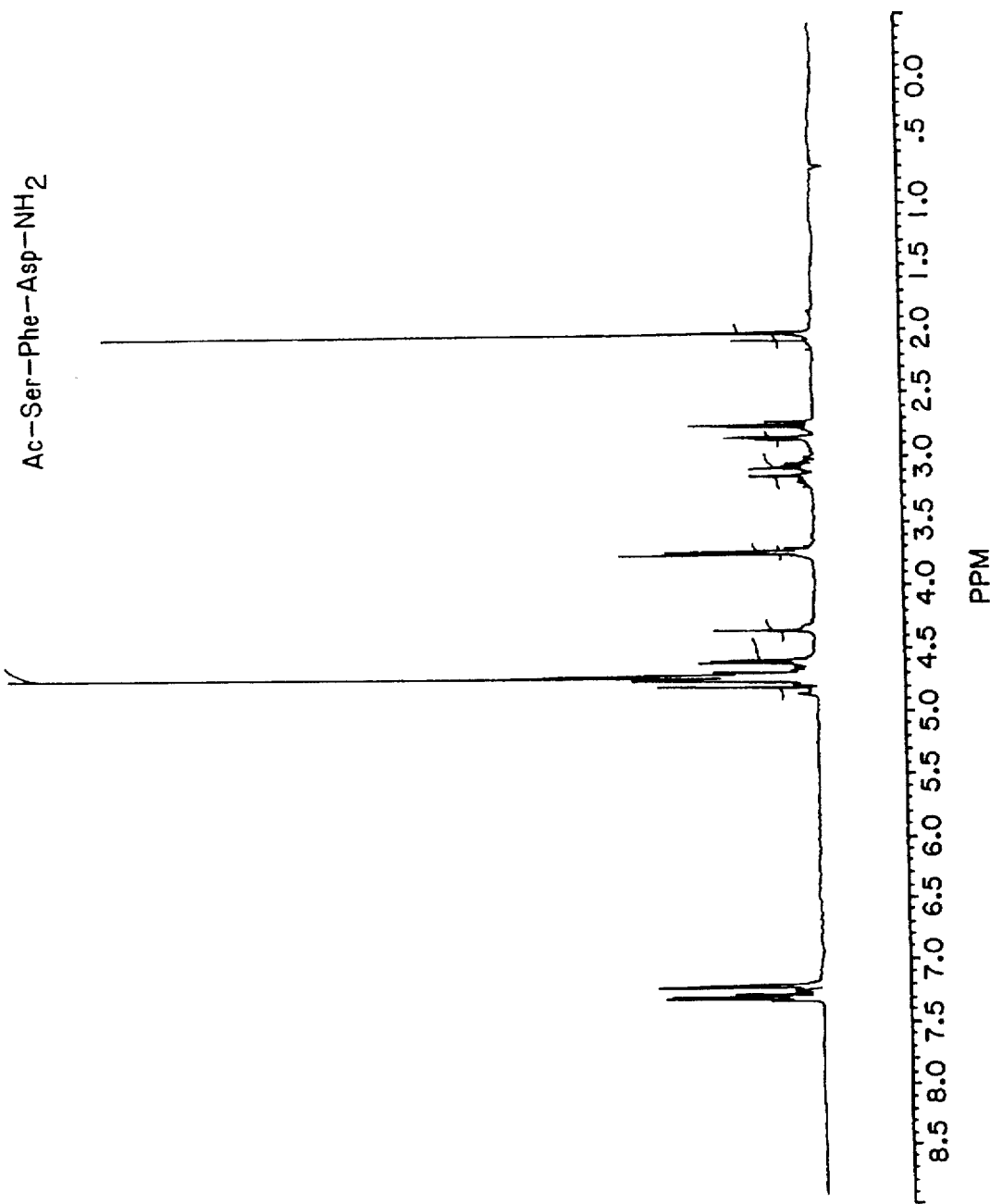
FIG. 21 is an NMR spectrum of Ac-Ser-Phe-Asp-NH$_2$.
Figure 22:
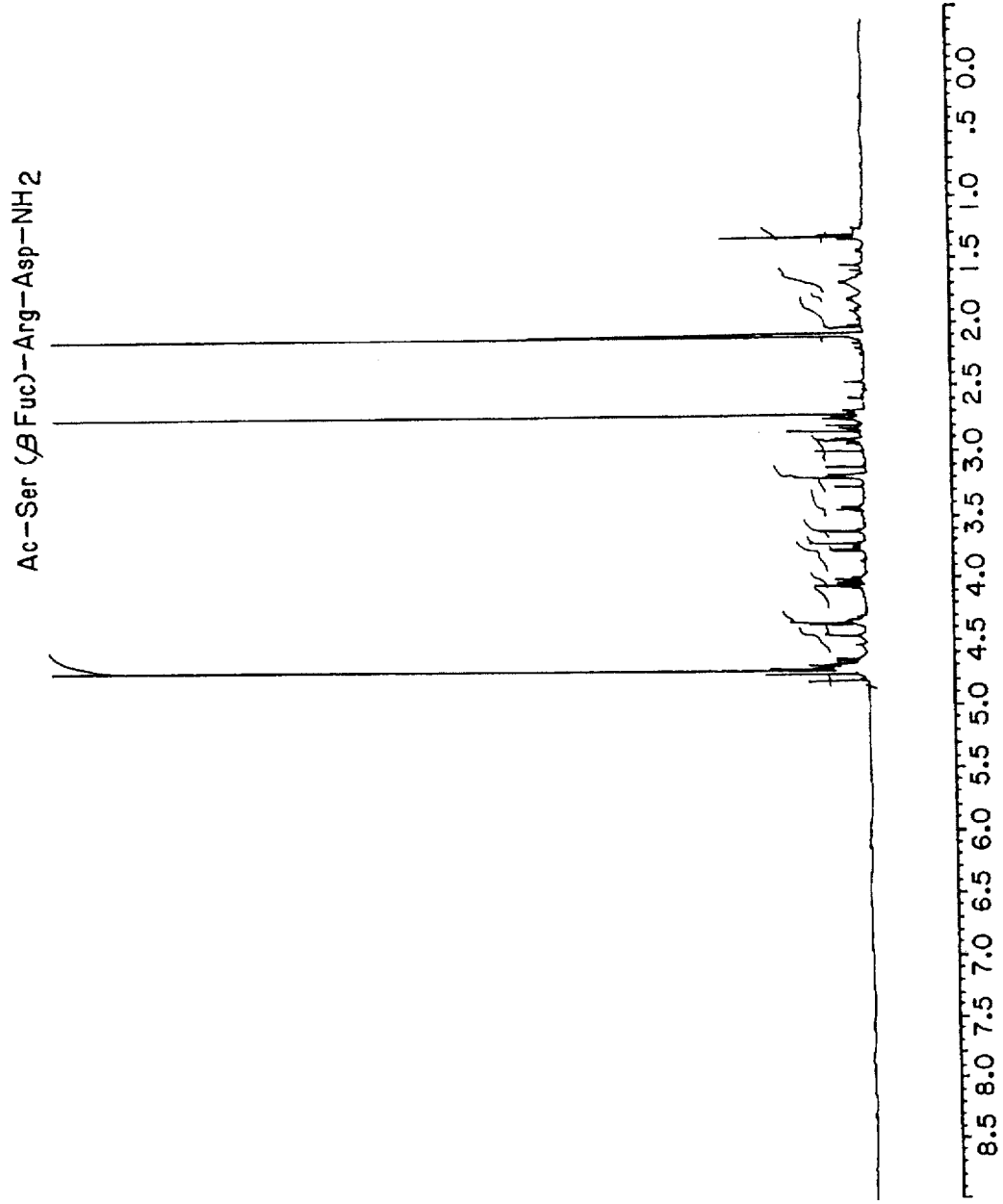
FIG. 22 is an NMR spectrum of Ac-Ser(β-L-Fuc)-Arg-Asp-NH$_2$.
Figure 23:
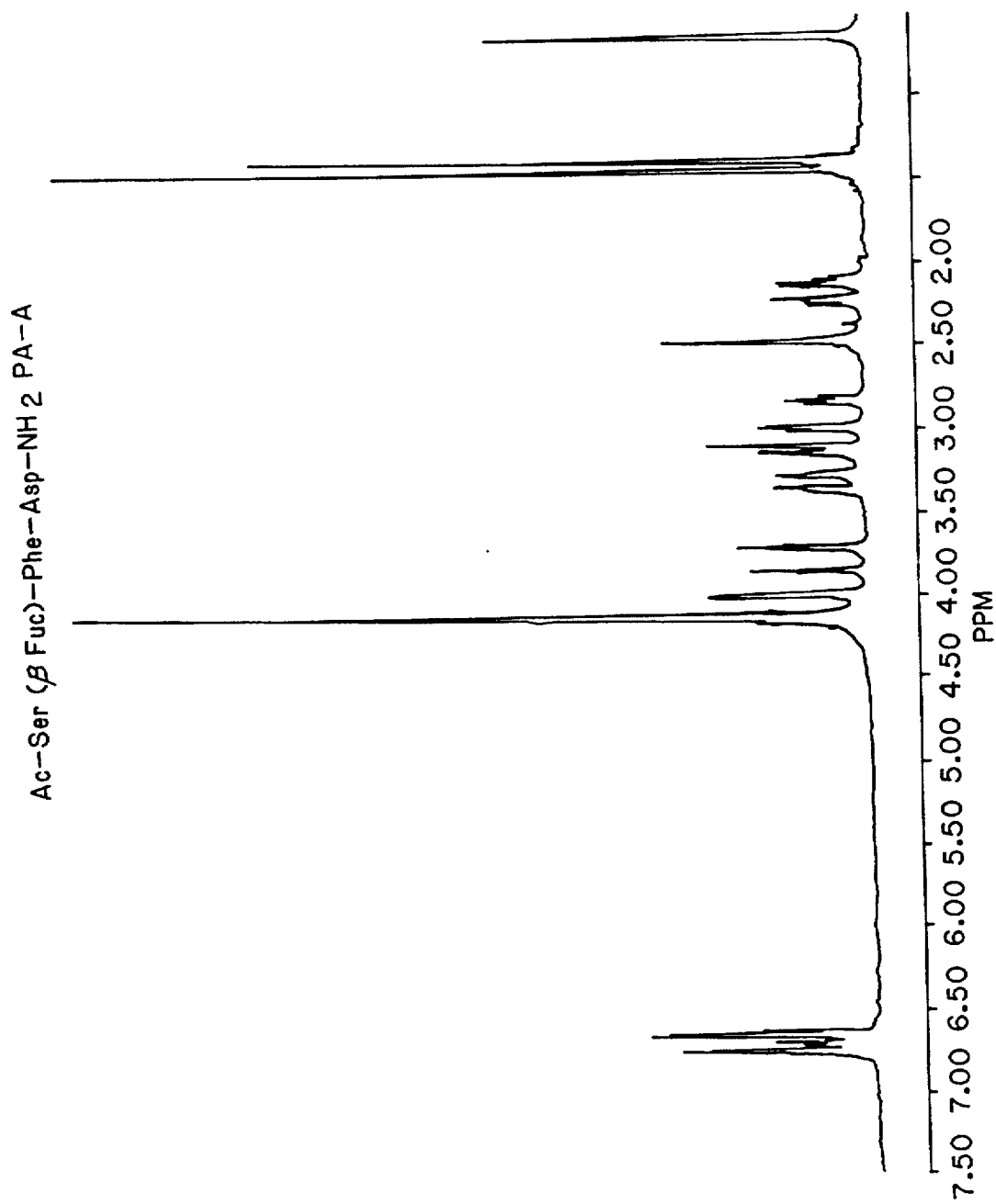
FIG. 23 is an NMR spectrum of Ac-Ser(β-L-Fuc)-Phe-Asp-NH$_2$.
Figure 24:
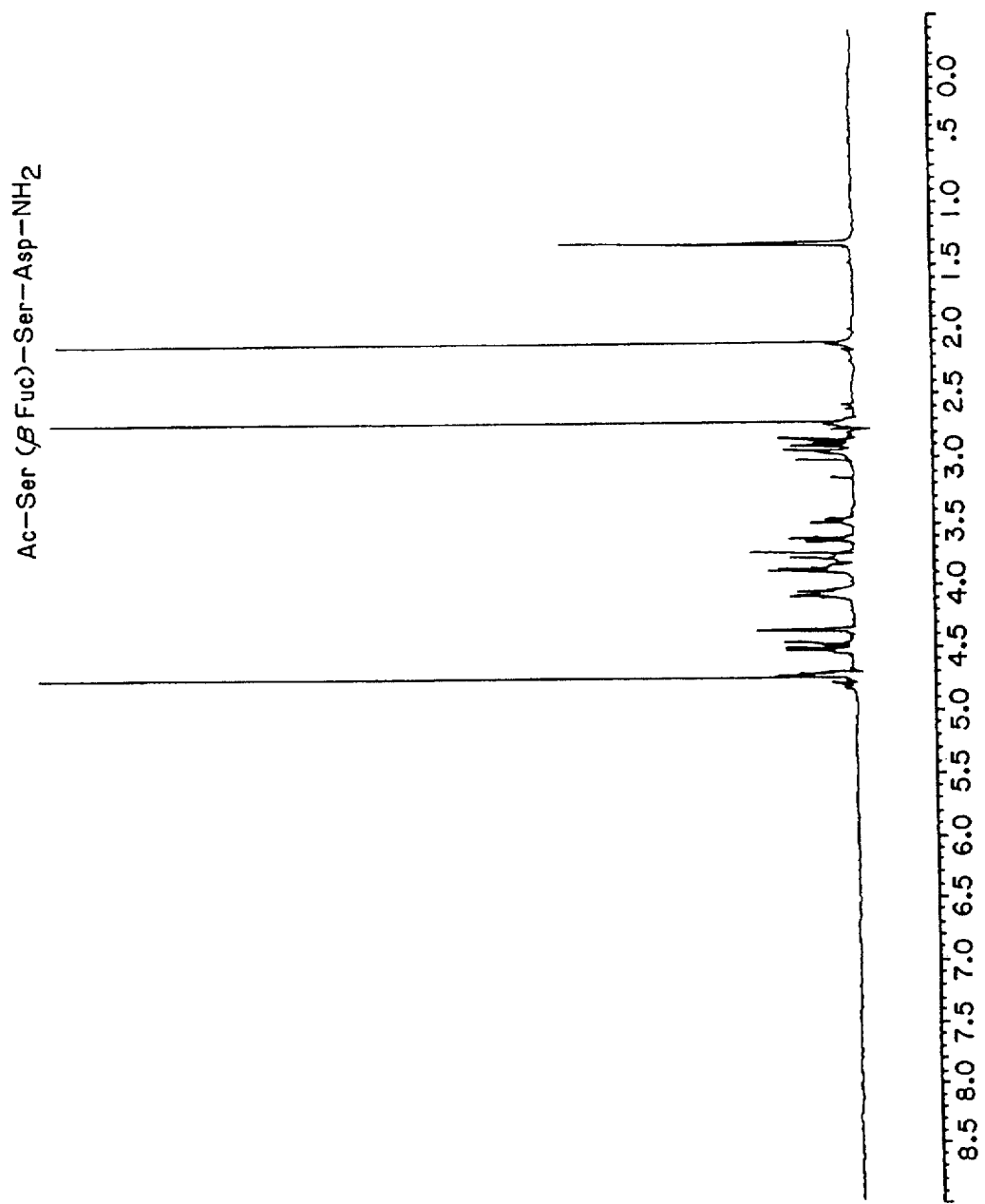
FIG. 24 is an NMR spectrum of Ac-Ser(β-L-Fuc)-Ser-Asp-NH$_2$.
Figure 25:
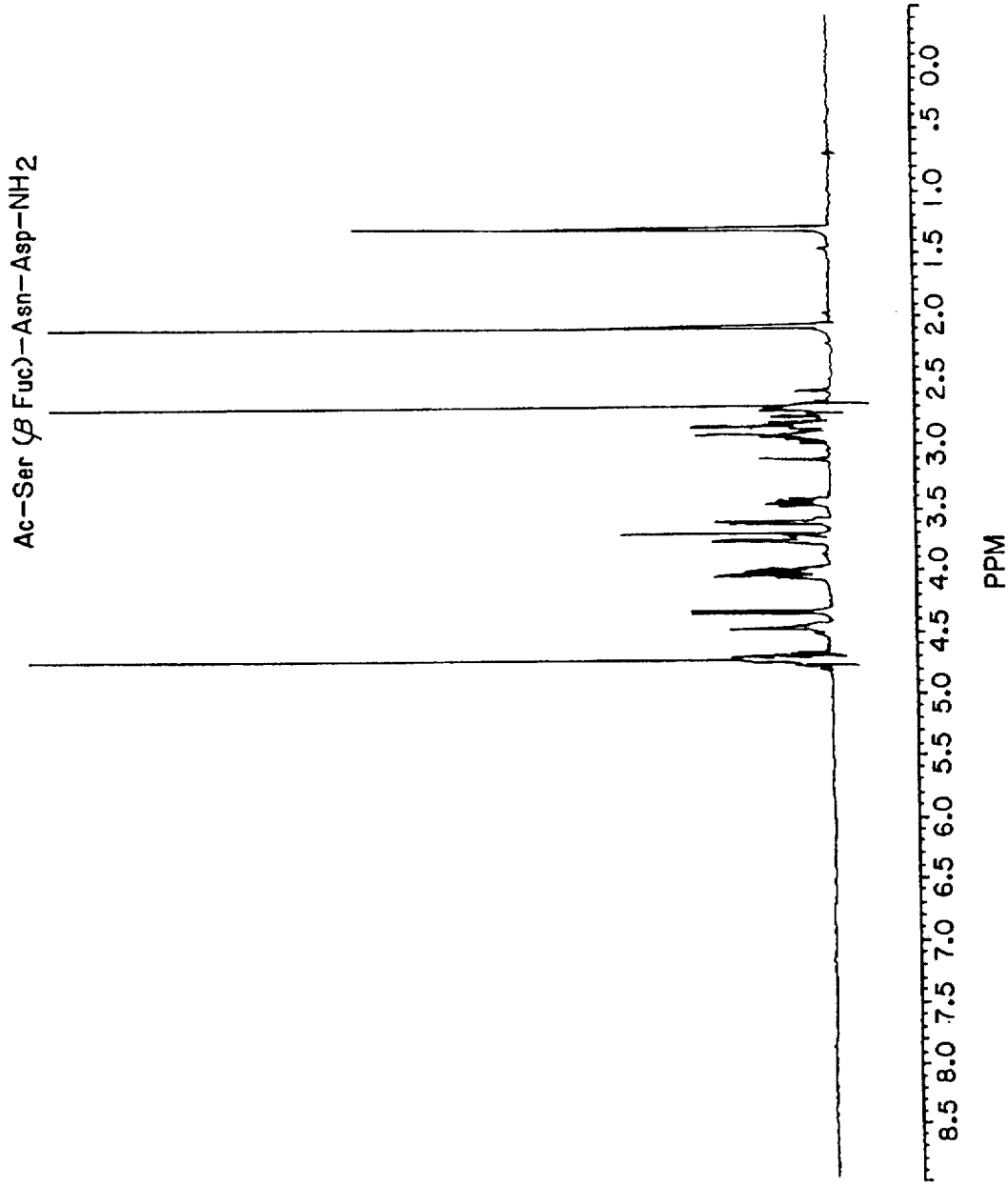
FIG. 25 is an NMR spectrum of Ac-Ser(β-L-Fuc)-Asn-Asp-NH$_2$.
Figure 26:
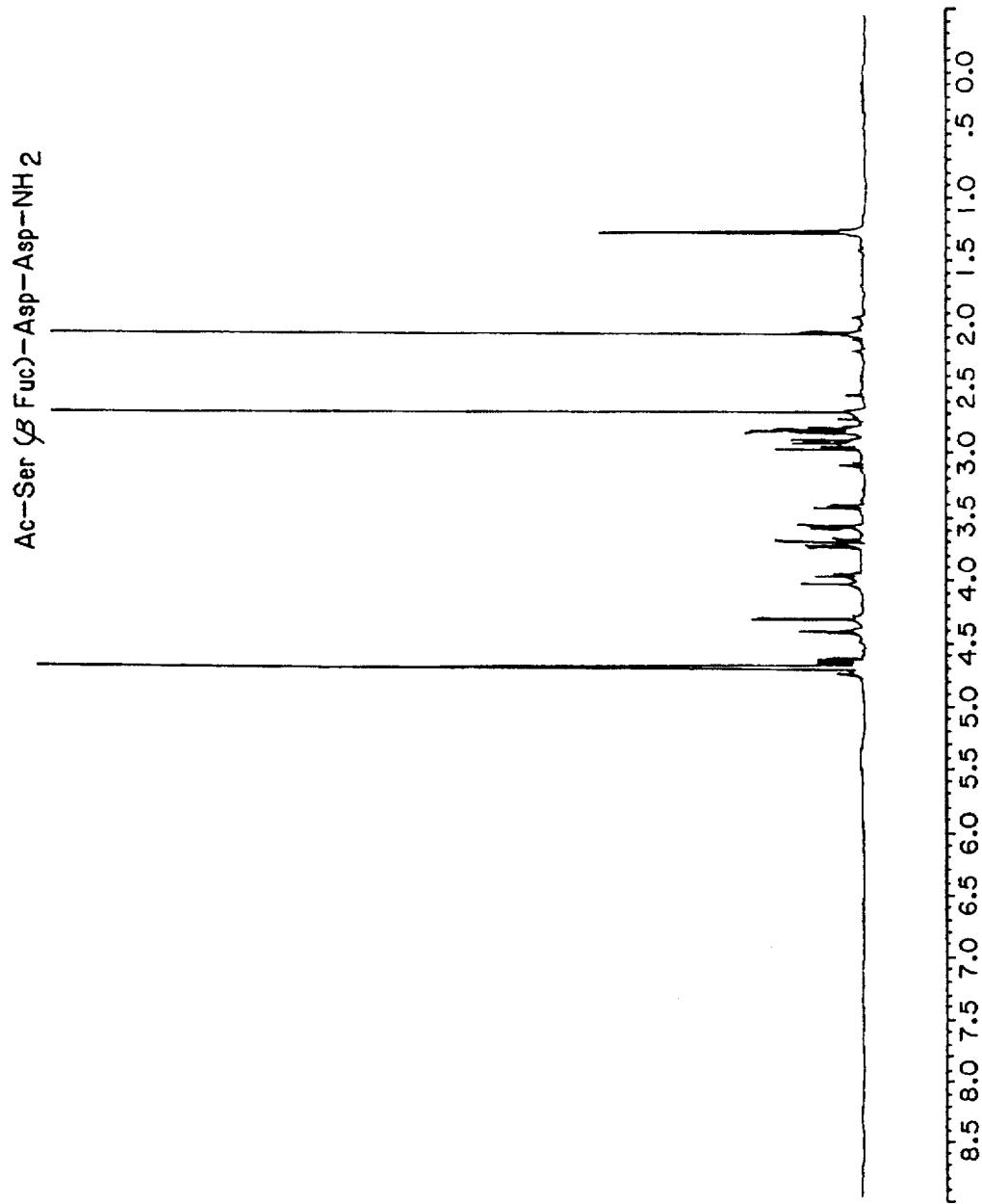
FIG. 26 is an NMR spectrum of Ac-Ser(β-L-Fuc)-Asp-Asp-NH$_2$.
Figure 27:
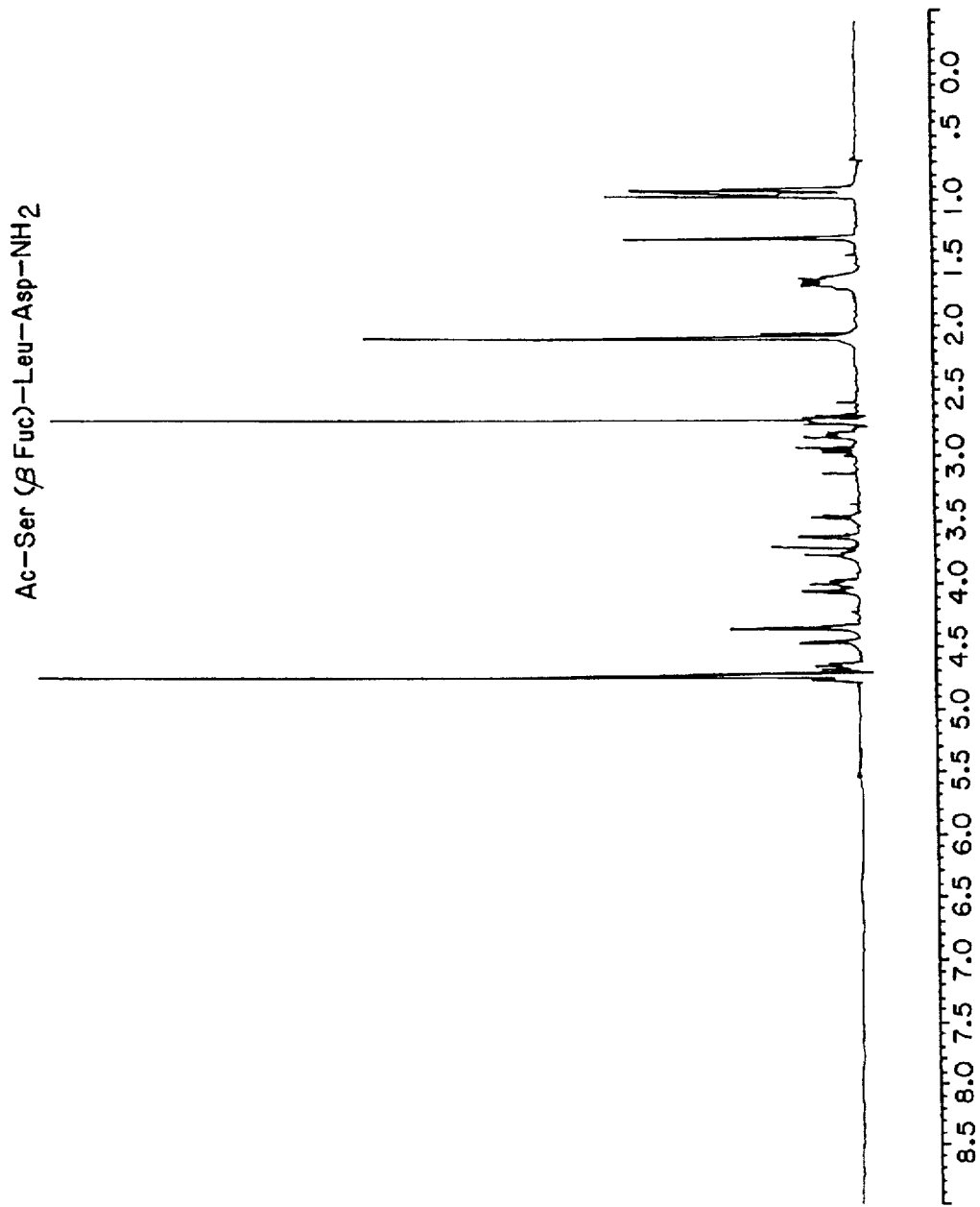
FIG. 27 is an NMR spectrum of Ac-Ser(β-L-Fuc)-Leu-Asp-NH$_2$.
Figure 28:
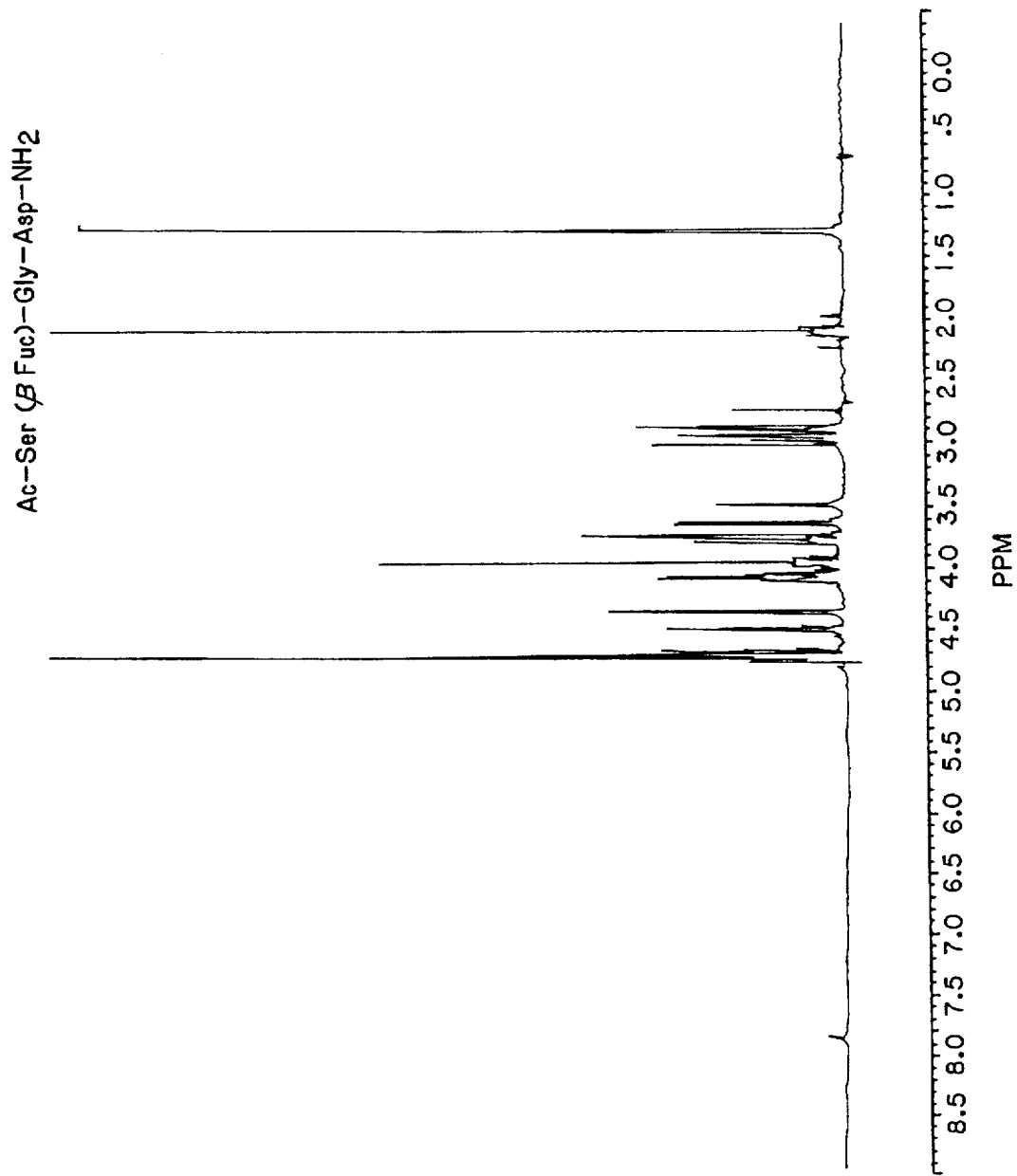
FIG. 28 is an NMR spectrum of Ac-Ser(β-L-Fuc)-Gly-Asp-NH$_2$.
Figure 29:
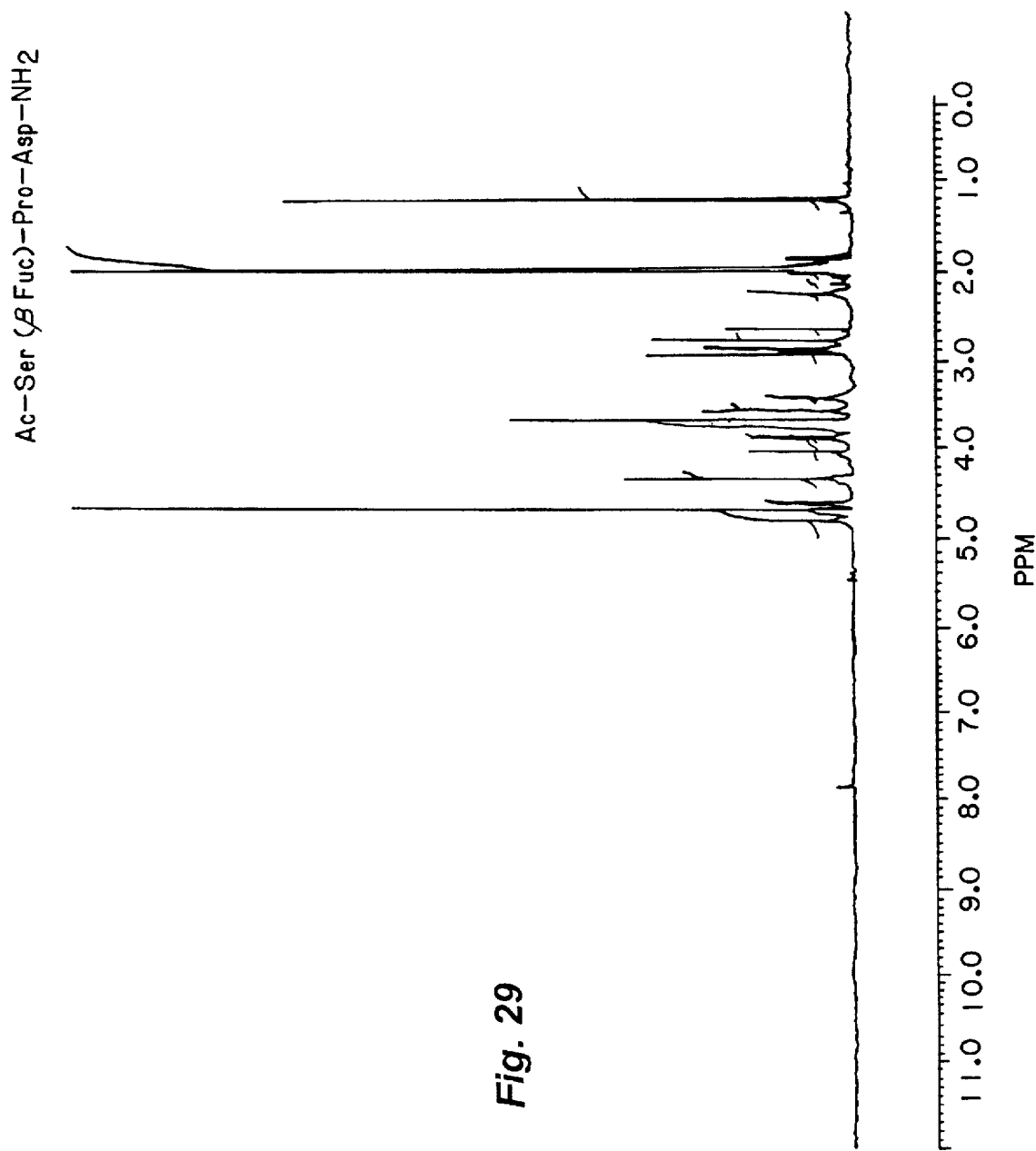
FIG. 29 is an NMR spectrum of Ac-Ser(β-L-Fuc)-Pro-Asp-NH$_2$.
Figure 30:
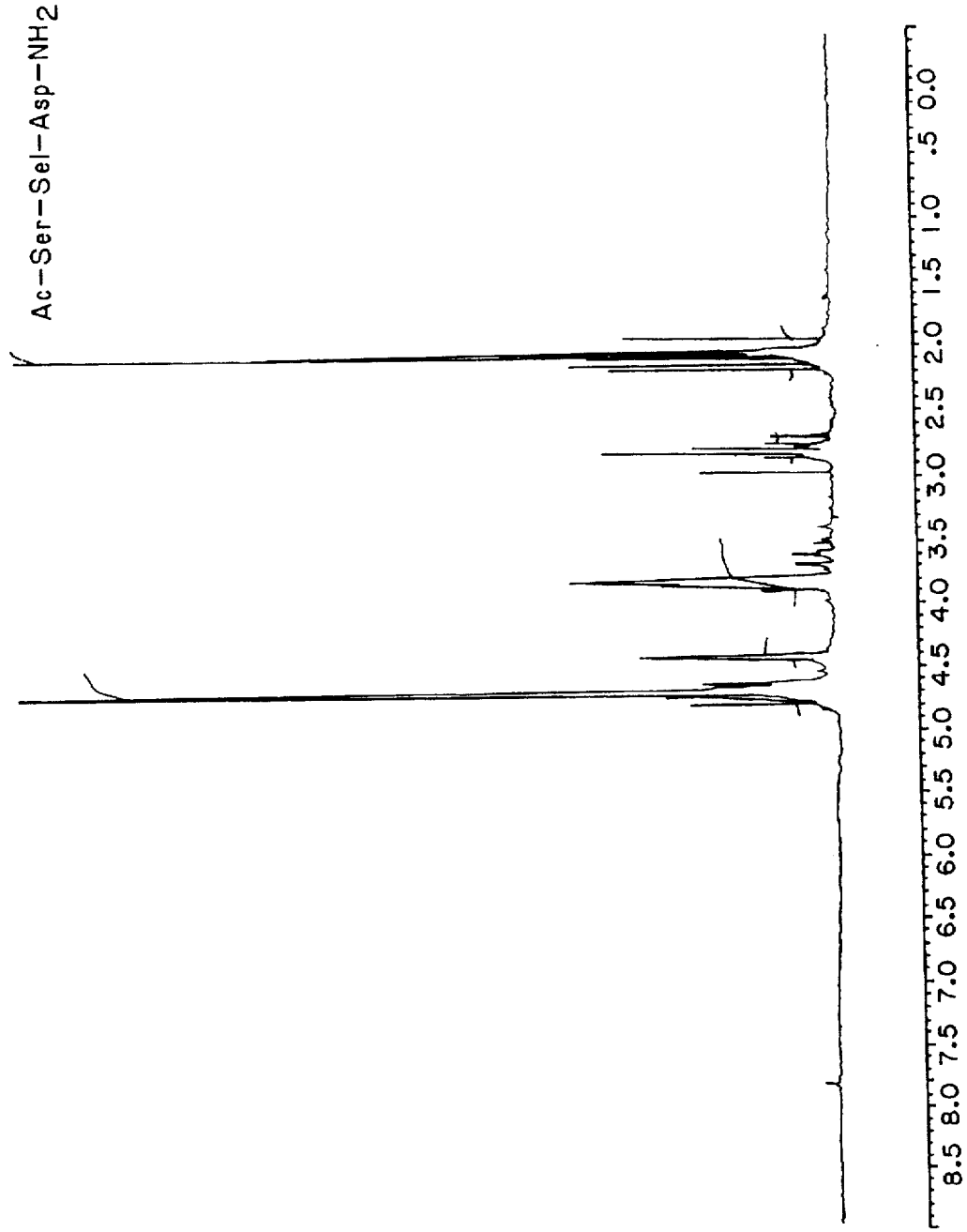
FIG. 30 is an NMR spectrum of Ac-Ser-Ser-Asp-NH$_2$.
Figure 31:
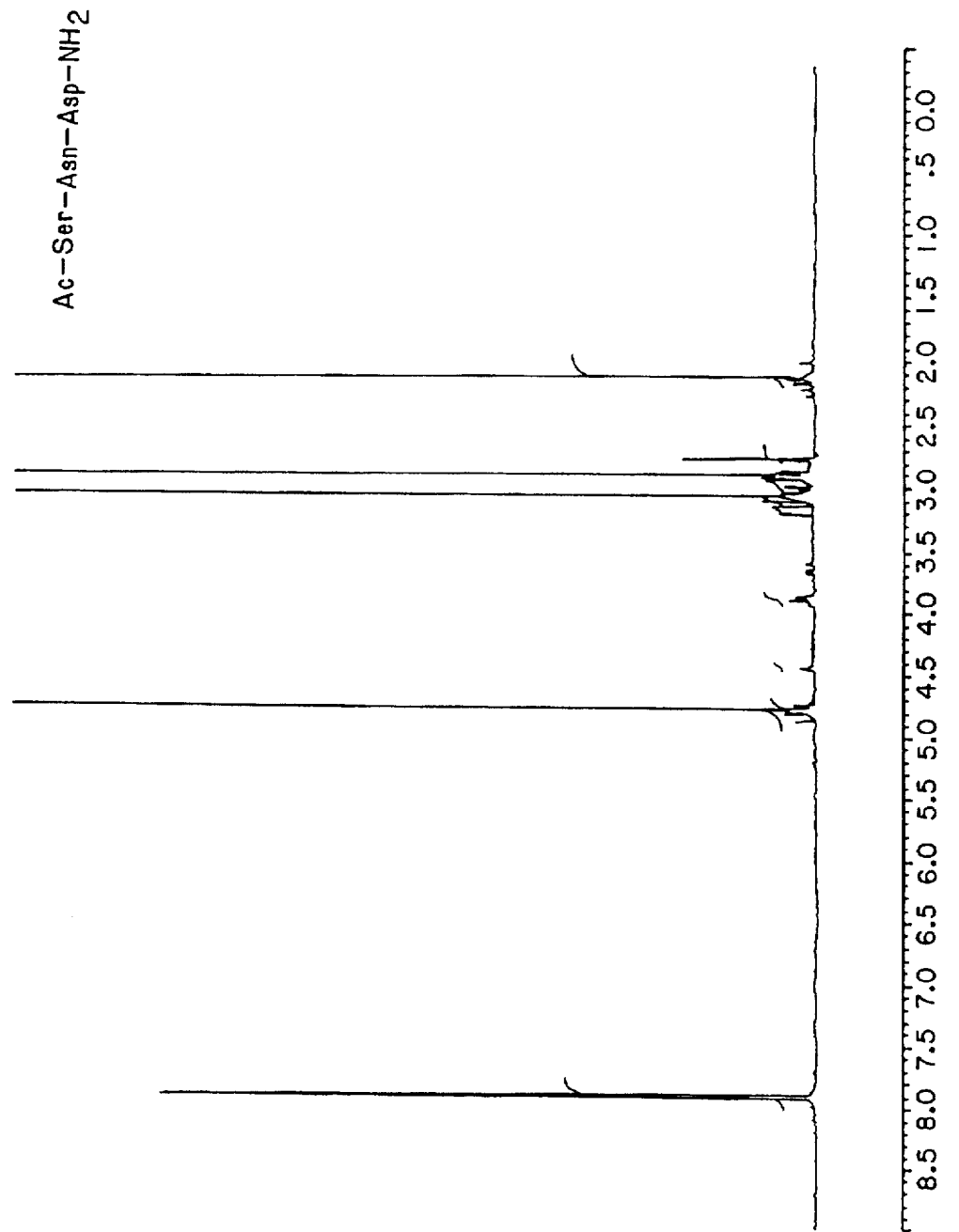
FIG. 31 is an NMR spectrum of Ac-Ser-Asn-Asp-NH$_2$.

FIG. 8 illustrates the differential effects of different concentrations of compounds C, D, E, F and H on the binding of L-selectin to 2,3 sLex glycolipid.

VII. Synthesis of selectin binding inhibitors

Figure 3:
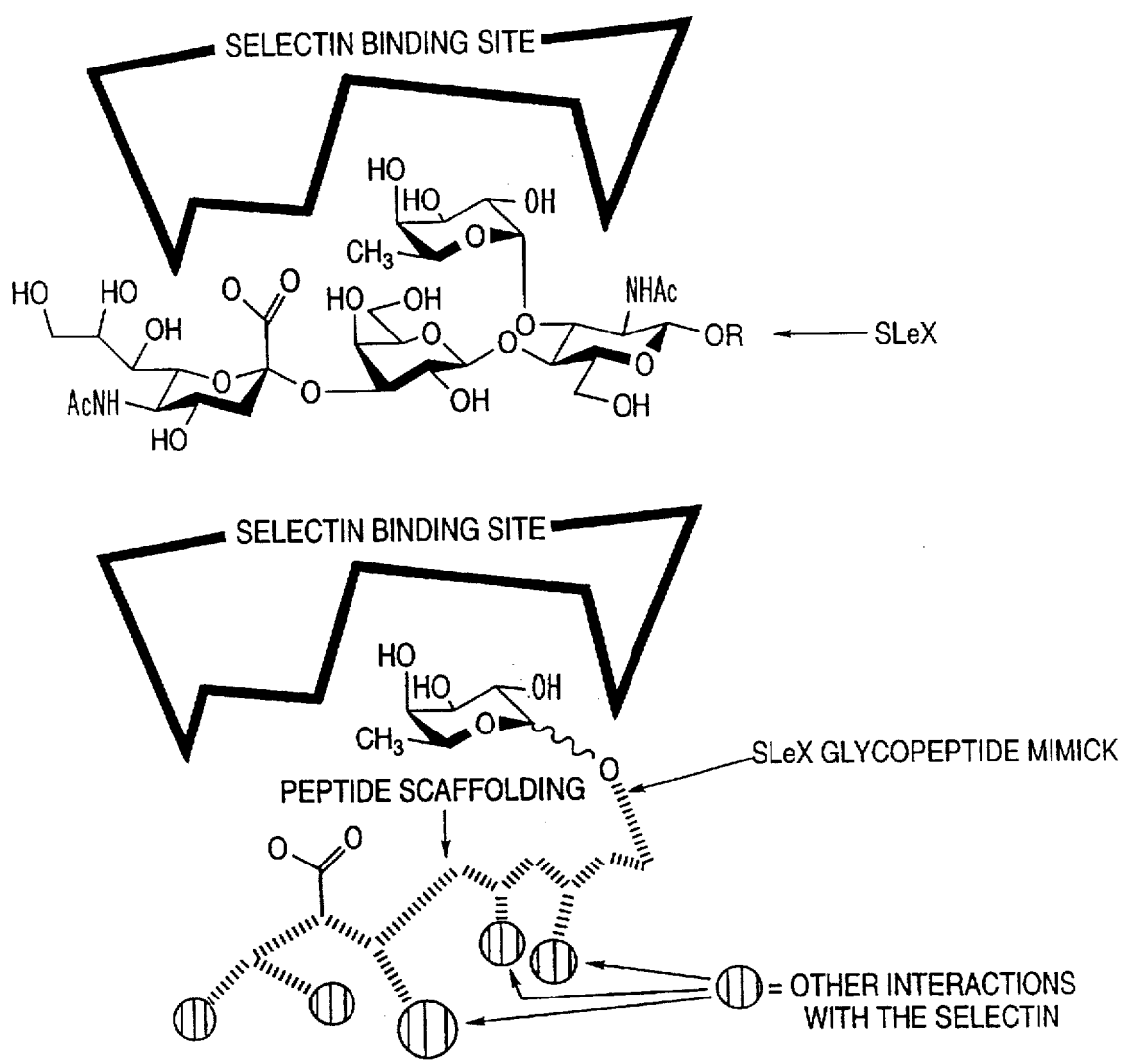
FIG. 3 shows a diagram of the interactions of SLeX and the SLeX glyco-peptide mimic with the selectin binding site.

A peptide derivative containing a fucose residue is prepared to mimic the binding of SLex to selectin binding sites (FIG. 3). Such a structure takes advantage of the interaction between selectin binding sites and the side chain carboxylic acid of aspartic acid, glutamic acid or the C-terminal amino acid present in all blocked peptides. The size of the SLex molecule suggests that peptide scaffolding could place a carboxy of a tripeptide on top that of the sialic acid and the OH group of a serine residue in a location similar to that of O-1 of the fucose residue. The glyco-peptide scaffolding is designed to interact favorably with the selectin binding site and under appropriate conditions, bind even tighter than the SLex molecule thereby acting as an inhibitor.

Additional Examples

In a similar manner as shown in Example VII, other peptide derivatives containing (multiple) carbohydrate residues are prepared to mimic the binding of SLex to selectin binding sites. Carbohydrate residues include mannose, glucose, N-acetylglucosamine, N-acetylgalactosamine, galactose and sialic acid.

In one embodiment the bio-oligomer is a glycopeptide. In another embodiment, the bio-oligomer is a glyco-oligonucleotide, in particular glyco-DNA or glyco-RNA. In yet a further embodiment, the bio-oligomer is a chimeric glyco-peptide/glyco-oligonucleotide.

The foregoing written specification is considered to be sufficient to enable one skilled in the art to practice the invention. Indeed, various modifications of the above-described modes for carrying out the invention which are obvious to those skilled in the art are intended to be within the scope of the following claims.

We claim:

1. A glycopeptide selected from the group consisting of:
Ac-Ser(α-L-Fuc)-Asp-Asp-NH$_2$,
Ac-Ser(α-L-Fuc)-Ser-Asp-NH$_2$,
Ac-Ser(α-L-Fuc)-Phe-Asp-NH$_2$,
Ac-Ser(α-L-Fuc)-Asn-Asp-NH$_2$,
Ac-Ser(α-L-Fuc)-Leu-Asp-NH$_2$,
Ac-Ser(α-L-Fuc)-Pro-Asp-NH$_2$,
Ac-Ser(β-L-Fuc)-Gly-Asp-NH$_2$,
Ac-Ser(β-L-Fuc)-Asp-Asp-NH$_2$,
Ac-Ser(β-L-Fuc)-Leu-Asp-NH$_2$,
Ac-Ser(β-L-Fuc)-Asn-Asp-NH$_2$,
Ac-Ser(α-L-Fuc)-Ala-Asp-NH$_2$,
Ac-Ser(β-L-Fuc)-Ala-Asp-NH$_2$,
Ac-Ser(β-L-Fuc)-Ser-Asp-NH$_2$,
Ac-Ser(β-L-Fuc)-Pro-Asp-NH$_2$,
Ac-Ser(α-L-Fuc)-Arg-Asp-OH,
Ac-Ser(α-L-Fuc)-Phe-Asp-OH,
Ac-Ser(α-L-Fuc)-Ser-Asp-OH,
Ac-Ser(α-L-Fuc)-Asn-Asp-OH,
Ac-Ser(α-L-Fuc)-Asp-Asp-OH,
Ac-Ser(α-L-Fuc)-Leu-Asp-OH,
Ac-Ser(α-L-Fuc)-Gly-Asp-OH,
Ac-Ser(α-L-Fuc)-Pro-Asp-OH,
Ac-Ser(β-L-Fuc)-Arg-Asp-OH,
Ac-Ser(β-L-Fuc)-Phe-Asp-OH,
Ac-Ser(β-L-Fuc)-Ser-Asp-OH,
Ac-Ser(β-L-Fuc)-Asn-Asp-OH,
Ac-Ser(β-L-Fuc)-Asp-Asp-OH,
Ac-Ser(β-L-Fuc)-Leu-Asp-OH,
Ac-Ser(β-L-Fuc)-Gly-Asp-OH,
Ac-Ser(β-L-Fuc)-Pro-Asp-OH,
Ac-Ser(α-L-Fuc)-Arg-Gly-OH,
Ac-Ser(α-L-Fuc)-Phe-Gly-OH,
Ac-Ser(α-L-Fuc)-Ser-Gly-OH,
Ac-Ser(α-L-Fuc)-Asn-Gly-OH,
Ac-Ser(α-L-Fuc)-Asp-Gly-OH,
Ac-Ser(α-L-Fuc)-Leu-Gly-OH,
Ac-Ser(α-L-Fuc)-Gly-Gly-OH,
Ac-Ser(α-L-Fuc)-Pro-Gly-OH,
Ac-Ser(β-L-Fuc)-Arg-Gly-OH,
Ac-Ser(β-L-Fuc)-Phe-Gly-OH,
Ac-Ser(β-L-Fuc)-Ser-Gly-OH,
Ac-Ser(β-L-Fuc)-Asn-Gly-OH,
Ac-Ser(β-L-Fuc)-Asp-Gly-OH,
Ac-Ser(β-L-Fuc)-Leu-Gly-OH,
Ac-Ser(β-L-Fuc)-Gly-Gly-OH,
Ac-Ser(β-L-Fuc)-Pro-Gly-OH,
Ac-Ser(β-L-Fuc)-Arg-Glu-NH$_2$,
Ac-Ser(α-L-Fuc)-Phe-Glu-NH$_2$,
Ac-Ser(α-L-Fuc)-Ser-Glu-NH$_2$,
Ac-Ser(α-L-Fuc)-Asn-Glu-NH$_2$,
Ac-Ser(α-L-Fuc)-Asp-Glu-NH$_2$,
Ac-Ser(α-L-Fuc)-Leu-Glu-NH$_2$,
Ac-Ser(α-L-Fuc)-Gly-Glu-NH$_2$,
Ac-Ser(α-L-Fuc)-Pro-Glu-NH$_2$,
Ac-Ser(β-L-Fuc)-Arg-Glu-NH$_2$,
Ac-Ser(β-L-Fuc)-Phe-Glu-NH$_2$,
Ac-Ser(β-L-Fuc)-Ser-Glu-NH$_2$,
Ac-Ser(β-L-Fuc)-Asn-Glu-NH$_2$,
Ac-Ser(β-L-Fuc)-Asp-Glu-NH$_2$,
Ac-Ser(β-L-Fuc)-Leu-Glu-NH$_2$, Ac-Ser(β-L-Fuc)-Gly-Glu-NH$_2$, and Ac-Ser(β-L-Fuc)-Pro-Glu-NH$_2$.

2. A glycopeptide as in claim 1 wherein the glycopeptide is Ac-Ser(α-L-Fuc)-Ala-Asp-NH$_2$.

3. A glycopeptide as in claim 1 wherein the glycopeptide is Ac-Ser(β-L-Fuc)-Ala-Asp-NH$_2$.

4. A glycopeptide as in claim 1, wherein the glycopeptide is Ac-Ser(α-L-Fuc)-Gly-Asp-NH$_2$.

5. A glycopeptide as in claim 1, wherein the glycopeptide is Ac-Ser(β-L-Fuc)-Arg-Asp-NH$_2$.

6. A glycopeptide as in claim 1, wherein the glycopeptide is Ac-Ser(α-L-Fuc)-Arg-Asp-NH$_2$.

7. A method of inhibiting selectin binding in a patient in need thereof, comprising the step of:

administering to the patient a therapeutically effective amount of a glycopeptide wherein the glycopeptide is selected from the group consisting of Ac-Ser(Fuc)-Ala-Asp-NH$_2$, Ac-Ser(Fuc)-Gly-Asp-NH$_2$ and Ac-Ser(Fuc)-Arg-Asp-NH$_2$.

* * * * *